(12) United States Patent
Chapman et al.

(10) Patent No.: US 10,596,335 B2
(45) Date of Patent: Mar. 24, 2020

(54) GAS SUPPLY APPARATUS WITH IMPROVED CONTROL

(75) Inventors: Andrew Michael Chapman, Auckland (NZ); Bruce William Potter, Auckland (NZ)

(73) Assignee: DEVX Tech IP Limited, Auckland (NZ)

( * ) Notice: Subject to any disclaimer, the term of this patent is extended or adjusted under 35 U.S.C. 154(b) by 253 days.

(21) Appl. No.: 12/161,793

(22) PCT Filed: Jan. 24, 2007

(86) PCT No.: PCT/NZ2007/000021
§ 371 (c)(1),
(2), (4) Date: Jul. 27, 2010

(87) PCT Pub. No.: WO2007/086766
PCT Pub. Date: Aug. 2, 2007

(65) Prior Publication Data
US 2010/0297593 A1   Nov. 25, 2010

(30) Foreign Application Priority Data
Jan. 24, 2006   (NZ) ........................................ 552009

(51) Int. Cl.
*A61M 16/00*   (2006.01)

(52) U.S. Cl.
CPC ... *A61M 16/0075* (2013.01); *A63B 2213/006* (2013.01)

(58) Field of Classification Search
CPC ..... A61B 5/0813; A61B 5/0833; A61B 5/091; A61B 5/097; A61B 5/14551; A61M 11/02; A61M 16/0051; A61M 16/0066; A61M 16/0096; A61M 16/024; A61M 16/026; A61M 16/0463; A61M 16/0627; A61M 16/0672; A61M 16/0677; A61M 16/0808; A61M 16/085; A61M 16/0858; A61M 16/10; A61M 16/101; A61M 16/1055; A61M 16/107; A61M 16/1095; A61M 16/12; A61M 16/16; A61M 16/161; A61M 16/18; A61M 16/20; A61M 16/202; A61M 16/204; A61M 16/205; A61M 16/208; A61M 16/209; A61M 16/22; A61M 2016/0021; A61M 2016/0024; A61M 2016/0027; A61M 2016/0039;

(Continued)

(56) References Cited

U.S. PATENT DOCUMENTS

| 5,237,987 A * | 8/1993 | Anderson | A61M 16/024 128/204.18 |
| 5,237,990 A * | 8/1993 | Psaros | A61M 16/18 128/203.12 |
| 5,365,922 A * | 11/1994 | Raemer | A61B 5/0833 128/202.22 |
| 5,558,083 A * | 9/1996 | Bathe | A61M 16/12 128/203.12 |
| 5,596,984 A * | 1/1997 | O'Mahony et al. | 128/205.24 |
| 5,682,877 A * | 11/1997 | Mondry | A61M 16/10 128/204.22 |

(Continued)

*Primary Examiner* — Annette Dixon
(74) *Attorney, Agent, or Firm* — Haynes and Boone LLP

(57) ABSTRACT

A gas supply apparatus with improved control is provided. The gas supply apparatus provides gas at an outlet junction. The apparatus includes a gas mixer for gasses from primary and secondary supplies to a given ratio. The apparatus also includes a gas reservoir supplied by the gas mixer. A tertiary supply valve is also included and connected in parallel with the reservoir. The tertiary supply valve is adapted to connect the outlet junction to a tertiary gas supply when gas is not being supplied to a mixer by the primary and/or secondary supply.

17 Claims, 13 Drawing Sheets

(58) Field of Classification Search
CPC .... A61M 2016/102; A61M 2016/1025; A61M 2016/1035; A61M 2202/0007; A61M 2202/0208; A61M 2202/0275; A61M 2202/03; A61M 2205/16; A61M 2205/3368; A61M 2205/3561; A61M 2205/502; A61M 2205/505; A61M 2205/7518; A61M 2205/8206; A61M 2230/005; A61M 2230/205; A61M 2230/40; A61M 2230/435; A61M 2230/437; A61M 2230/63; Y02C 20/10
USPC .......... 434/262; 128/205.26, 202.12, 205.11, 128/204.23, 203.14, 203.12, 204.21
See application file for complete search history.

(56) References Cited

U.S. PATENT DOCUMENTS

| | | | | |
|---|---|---|---|---|
| 5,752,506 | A * | 5/1998 | Richardson | A61M 16/0096 128/204.18 |
| 6,139,506 | A * | 10/2000 | Heinonen | A61B 5/091 600/529 |
| 6,279,574 | B1 * | 8/2001 | Richardson | A61M 16/0096 128/204.18 |
| 6,371,114 | B1 * | 4/2002 | Schmidt | A61M 16/026 128/204.23 |
| 7,681,574 | B2 * | 3/2010 | Heinonen | A61B 5/0813 128/204.18 |
| 2006/0185669 | A1 * | 8/2006 | Bassovitch | 128/202.12 |
| 2007/0193579 | A1 * | 8/2007 | Duquette et al. | 128/204.18 |
| 2010/0137380 | A1 * | 6/2010 | Maybaum | 514/363 |

* cited by examiner

GAS SUPPLY APPARATUS WITH IMPROVED CONTROL

FIELD OF THE INVENTION

The present invention relates to apparatus for supplying a variable mix of gases. In particular it relates to apparatus for supplying a variable mix of breathable gases. Further in particular it relates to an apparatus for supplying a subject with gas having a variable level of oxygen. Yet further in particular it relates to an apparatus for applying hypoxic training to a subject.

DESCRIPTION OF THE PRIOR ART

Hypoxic training involves supplying a subject with hypoxic air to place a beneficial stress on the subject's pulmonary system. Generally this type of training is applied intermittently to allow the subject to recover from the stress by breathing normoxic air.

In this context, hypoxic air is air with a modified oxygen content and normoxic air is ambient atmospheric air. Hypoxic air has reduced oxygen levels compared to normoxic air.

The benefits of hypoxic training were discovered by observation of the physiology of subjects living in a ratified atmosphere at altitude. For this reason, hypoxic training is often referred to as simulated altitude training.

Apart from the obvious convenience of having the benefit of altitude training at lower altitudes, hypoxic training apparatus also allows subjects to carry out other types of training in low altitude normoxic air in between simulated altitude training sessions.

Currently, hypoxic training is generally limited to use by elite subjects because: the capital cost of the equipment is generally high; the running cost of the equipment is generally high; and/or the training equipment involves a level of risk to the health or safety of the subject.

Some existing hypoxic training apparatus provides a subject with a mix of normoxic air and nitrogen, or a similar inert gas, to create a hypoxic air mix to supply to the subject.

Most existing hypoxic apparatus requires feedback from an oxygen analyser to control the various valves that control the ratio of air and nitrogen supplied to a subject. The feedback provided by the oxygen analyser is used to control proportional valves which determine the mix of air and nitrogen and, thereby, the oxygen content supplied to the subject. Feedback from the oxygen analyser is necessary due to the difficulty in positively and precisely controlling the state of the valve and thereby the mix of gases. This difficulty arises due to such factors as mechanical hysteresis.

An oxygen analyser is a sophisticated and expensive piece of equipment to include in the apparatus. An oxygen analyser obviously adds considerable cost in the manufacture and maintenance of the apparatus. Also, the effectiveness of feedback from the oxygen analyser is limited by the response time of the oxygen analyser, which can be considerable in terms of timeframes for feedback electronic systems.

Generally, valve systems used in hypoxic apparatus to control the rate of gas flow to a venturi for example, consist of one or more proportional valves. A proportional valve is one which includes an aperture the size of which is adjusted to adjust the flow through the valve. The flow is proportional to the size of the aperture. Generally, proportional valves are expensive and may involve characteristics which make them difficult to control, such as mechanical hysteresis. In most cases, and especially where relatively imprecise proportional valves are used, sophisticated feedback of the level of oxygen delivered to the subject is required.

The need for conventional hypoxic training apparatus to use sophisticated feedback mechanisms and to use expensive proportional valves is due to the intrinsic risk involved in supplying a subject with hypoxic air with reduced oxygen levels. Therefore, conventional hypoxic training apparatus has a high capital cost and high maintenance costs.

Some hypoxic training apparatus operates by mixing ratios of compressed air and compressed nitrogen. This carries with it the cost of supplying compressed air in addition to compressed nitrogen.

Some systems overcome the need to supply both compressed air and compressed nitrogen by the use of a venturi. A venturi is a conduit with a restricted passage. Accordingly to Bernoulli's equation, the pressure within the restricted portion of a venturi can be determined by the pressure of the gas feed into the conduit and by the dimensions of the restricted portion. If an inlet for a second gas is included in the side of the venturi, at the restricted portion, then it is possible to pre-determine a mix of the two gases by the feed pressures and dimensions of the venturi. That is, the feed pressure of the first gas and dimensions of the venturi determine the pressure at the restricted portion, or neck, of the venturi. By controlling the feed pressure and dimensions of the venturi, it is possible to create a partial vacuum in the neck of the venturi which can draw in a second gas which will mix with the first gas. The gas drawn into the neck of the venturi can be atmospheric air. This avoids the need to supply compressed air.

Some hypoxic training apparatus involves re-breathing inhaled air then treating air supplied to the subject. This apparatus generally does not allow for any active control of the level of oxygen to be supplied. These systems introduce an obvious risk in a subject losing consciousness while being supplied with hypoxic air, and failing to remove themselves from the hypoxic air supply.

Given either the risk or expense associated with hypoxic systems, it is not surprising that the benefits of hypoxic training have not reached far beyond use for elite subjects such as athletes or race horses.

Some conventional hypoxic training schemes are typically controlled by way of the content of oxygen that is supplied to a subject. This is, a subject may be supplied with 9-12% oxygen for given intervals. However the applicant has observed that given oxygen contents will produce different $SPO_2$ levels in different subjects. This means that a training system does not necessarily induce an ideal training $SPO_2$ in a given subject. The result may be training sessions that are less effective, that may take longer or that may even be dangerous.

Conventionally, hypoxic training systems are calibrated to supply given ratios of normoxic air and an ambient gas such as nitrogen. Nitrogen is generally supplied commercially in a high purity mix in which oxygen constitutes the main impurity. It is well known that there is trade off between, the purity of nitrogen and the time taken to 'generate' the nitrogen from ambient air. Additional processing time leads to additional costs associated with the nitrogen supply. For example, 95% nitrogen and 5% oxygen supply is cheaper than a 99% nitrogen and 1% oxygen supplied. However, 99% is the industry standard for bottled supplies of nitrogen.

A characteristic of the mammalian body is that once a hypoxic supply is replaced with a normoxic supply, the subject's saturated oxygen levels—$SPO_2$ level—'bounces', or over compensates, relatively high. Having a subject's SPO$_2$ level bounce to a relatively high level is not optimal for hypoxic training session. It would be advantageous to have a system where periods of relatively high SPO$_2$ 'bounce' levels are avoided during a hypoxic training session.

Some existing hypoxic training systems for multiple users have switches which switch hypoxic supply between subjects to create the intermittent supply of hypoxic air. A normoxic supply is switched to one subject when the hypoxic supply is switched to other subjects. Typically, pairs of subjects are involved and each subject has equal periods of normoxic and hypoxic supply. Therefore, these systems apply equal periods of hypoxic and normoxic air to each subject. The applicant has observed that non-equal periods of hypoxic and normoxic supply may result in training sessions with improved results or with reduced session times for similar results. Such non-equal periods are not possible with these multi-user systems.

A hypoxic training apparatus may be supplied either directly from a nitrogen generator or with commercially bottled nitrogen. In this case, the hypoxic training apparatus, which must be carefully calibrated, will generally be calibrated to the mix of nitrogen and oxygen that is commercially available in bottled supply. This may be 99% for example. Any cost saving in setting of an on-site generator to produce only 95% pure nitrogen is outweighed by the cost and complexity of re-calibrating the hypoxic training apparatus.

It is an object of the present invention to provide a hypoxic training apparatus that is readily recalibrated for commercially bottled or on-site generated nitrogen, or at least to provide the public with a useful choice in hypoxic training apparatus.

It is an object of the present invention to provide a relatively low cost alternative to existing hypoxic training apparatus, or at least to provide the public with a useful choice.

It is a further object of the present invention to provide a hypoxic training apparatus that is relatively safe to use and/or is suitable for use with minimal supervision, or at least to provide the public with a useful choice in hypoxic training apparatus.

It is a further object of the present invention to provide a hypoxic training apparatus that allows relatively precise control of the mix of nitrogen and air, or at least to provide the public with a useful choice in hypoxic training apparatus.

It is a further object of the present invention to provide a gas mixing apparatus that overcomes or mitigates problems or shortcomings associated with existing hypoxic training apparatus, or at least to provide the public with a useful choice in gas mixing apparatus.

It is a further object of the present invention to provide a low cost flow valve, or at least to provide the public with a useful choice in flow valves.

It is a further object of the present invention to provide an improved method of applying hypoxic training or at least to provide the public with a useful choice in hypoxic training methods.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken, to mean an inclusion of not only the listed components it directly references, but also other non-specified components or elements. This rationale will also be used when the term 'comprised' or 'comprising' is used in relation to one or more steps in a method or process.

As used herein the term 'pulse' refers broadly to a valve spending a given interval in a given state.

As used herein the term 'pulse width modulation', or similar, relates to a technique whereby the a device or signal is pulsed between two states and the widths of pulses, as seen over time, are modulated to vary the proportion of time, over a given interval, that the device or signal spends in a given state.

Further aspects and advantages of the present invention will become apparent from the ensuing description which is given by way of example only.

SUMMARY OF THE INVENTION

According to one aspect of the present invention there is provided a gas supply apparatus which provides gas to an outlet junction, the apparatus comprising:
- a gas mixer adapted to mix gas from at least primary and secondary gas supplies to a given ratio;
- a gas reservoir supplied by the gas mixer, and connected to the outlet junction;
- a tertiary supply gas valve connected to the outlet junction in parallel with the reservoir, wherein the tertiary supply gas valve is adapted to connect the outlet junction to a tertiary supply of gas when gas is not being supplied to the mixer by the primary and/or secondary supply.

This means that, when the first and/or second supply is disconnected to the mixer, the outlet junction is supplied by the third supply and also by the reservoir. The gas available at the outlet junction is a combination of gas from the reservoir and gas from the third supply. This occurs until the reservoir is depleted at which point the gas available at the outlet junction is gas from the third supply only. If gas from the mixer is different from gas from the third supply, a gradual change will be affected, from a combination of gases through to gas only from the third supply.

Preferably, the gas supplied via the secondary and tertiary supplies comprise ambient atmosphere.

Thus, the present invention also removes a constraint from the design of the mixing valve, namely that it can supply enough air from the secondary supply of the gas mixer to the outlet junction as may be required. If the gas supply apparatus is supplying hypoxic air to a subject, they will be supplied enough air, through the tertiary supply valve, even though the most efficient or economical choice of gas mixer may not supply sufficient air from the secondary supply once the primary supply has been shut-off.

Preferably, the gas supplied via the primary supply comprises a supply of nitrogen.

Preferably, the supply of nitrogen comprises a pressurised supply.

Preferably, the gas mixer is adapted to mix air at the secondary supply with nitrogen at the primary supply so as to provide air with a given oxygen content.

Preferably, the gas mixer is adapted to provide hypoxic air.

If nitrogen at the first supply is suspended, the outlet junction is supplied with a combination of normoxic air at the third supply and hypoxic air from the reservoir. This combination is immediately less hypoxic than the mix previously delivered from the gas mixer. This combination then gradually becomes less hypoxic as the reservoir of hypoxic air is depleted. Eventually only normoxic air, from the third supply via the alternative supply gas valve, is available at the outlet junction. A gradual transition from hypoxic to normoxic air mitigates a tendency of the mammalian body to overcompensate, or 'bounce' its blood saturation levels. This allows improved effectiveness of hypoxic training that may utilise the gas supply apparatus.

Preferably, the tertiary gas supply valve includes a control input connected to the primary supply, and wherein the tertiary gas supply valve is adapted to be closed only when gas is being supplied to the control input by the primary supply.

Preferably, the gas reservoir includes a debatable bag.

Preferably, the gas reservoir has a capacity chosen to be greater than the volume of gas provided by the gas mixer in one second.

Preferably, the gas reservoir has a capacity chosen to be greater than the volume of gas provided by the gas mixer in 6 seconds.

Preferably, the gas reservoir has a capacity of substantially 1.5 litres or more.

Preferably, the gas reservoir has a capacity of substantially 4 litres or more.

Preferably, the gas reservoir includes a controller adapted to control the gas mixer.

Preferably, the controller is adapted to receive a signal from a pulse oximeter, said signal indicating a blood oxygen saturation of a subject.

Preferably, the controller is adapted to read calibration data defining settings for the gas mixer, said settings corresponding to given oxygen contents in air provided by the gas mixer.

Preferably, the controller is adapted to select an oxygen content in response to the received pulse oximetry signal.

Preferably, the controller is configured to monitor at least one time dependent aspect of the pulse oximetry signal.

Preferably, said time dependent aspect includes a time to reach a first predetermined level.

Preferably, said time dependant aspect is a time to reach a second predetermined level.

Preferably, at least one time dependent aspect includes whether or not a first predetermined level has been reached within a predetermined time interval.

Preferably, the controller is adapted to adjust the selected oxygen content if the first predetermined level is not reached within the predetermined time interval.

Preferably, the controller is adapted to reduce the oxygen content of gas if the first predetermined level is not reached within the predetermined time interval.

Preferably, the controller is adapted to cause, the tertiary supply valve to open, for a predetermined interval once the first predetermined level of the pulse oximetry signal has been reached.

Preferably, said at least one time dependant aspect includes whether or not a second predetermined level has been reached within a second predetermined time interval.

Preferably, the controller is adapted to increase the oxygen content of gas delivered at the reservoir if the second predetermined time interval has been reached within the second predetermined time interval.

Preferably, at least one time dependent aspect includes a rise time.

Preferably, the controller is adapted to adjust an oxygen content value if the rise time meets predetermined criteria.

Preferably, the controller is adapted to adjust the selection of an oxygen content downward if the rise time is less than a predetermined level.

Preferably, said time dependent aspect includes a fall time.

Preferably, the controller is adapted to adjust an oxygen content value if the fall time meets predetermined criteria.

Preferably, the controller is adapted to adjust the selection of oxygen content upwards, if the fall time is less than a predetermined value.

Preferably, the controller is adapted to read hypoxic training session data which defines intervals of supply of hypoxic air and wherein the controller is also adapted to control the supply of nitrogen to the gas mixer according to those intervals.

Preferably, said intervals of supply of hypoxic air comprise approximately 70% of the total time from the start of the first said interval of supply to the end of the last said interval of supply.

Preferably, the hypoxic training data defines a number of alternating intervals of hypoxic and normoxic supply.

Preferably, the controller is adapted to monitor said signal from a pulse oximeter and to select a given oxygen content so as to provide feedback control of said signal from a pulse oximeter.

Preferably, the controller is adapted to receive a signal from a pulse oximeter, said signal indicating a heart beat rate.

Preferably, the controller is adapted to read pulse oximetry data defining criteria for supplying hypoxic air from the outlet junction.

Preferably, the controller is adapted to allow hypoxic air to be supplied to the reservoir only if said criteria is met by the received pulse oximetry signal.

Preferably, the controller is adapted to read pulse oximetry data including an initiating minimum pulse oximetry value below which supply of hypoxic air should not be initiated.

Preferably, the controller is adapted to read pulse oximetry data including a suspension minimum pulse oximetry value below which supply of hypoxic air should be suspended.

Preferably, the controller is adapted to read pulse oximetry data including a resumption minimum pulse oximetry level below which said mix should not be resumed after being suspended.

Preferably, the minimum resumption pulse oximetry value is higher than the minimum suspension poise oximetry level.

Preferably, the controller is adapted to read hypoxic training session data defining intervals of supply of hypoxic air.

Preferably, the controller is adapted to read training session data defining any one or any combination of the following parameters associated with an identifier assigned to at least one subject:
duration of periods of hypoxic supply;
duration of periods of normoxic supply;
duration of combined hypoxic and normoxic periods;
number of sessions of hypoxic and normoxic supply;

number of cycles of periods of hypoxic intervals supplied in a given session.

Preferably, the controller is adapted to generate a signal for a display, said signal representing at least one of said time dependent aspects.

Preferably, the gas mixer comprises:
a mixing volume;
a primary inlet provided for the mixing volume;
a secondary inlet provided for the mixing volume;
and an outlet provided for the mixing volume,
wherein said secondary inlet includes a valve which is adapted to be operated by a pulse width modulation driver adapted to pulse width modulate the valve between two flow states to achieve a given flow state through the secondary inlet.

Preferably, said mixing volume comprises a venturi.

Preferably, said secondary inlet communicates substantially with a restricted passage of the venturi.

Preferably, the primary inlet includes a valve which is adapted to be operated by a pulse width modulation driver to pulse width modulate the valve between two flow states to achieve a given flow state through the primary inlet.

Preferably, the fluid mixing apparatus includes a controller adapted to provide a control signal for a pulse width modulation driver(s).

Preferably, pulse width modulation of each of the valves included with primary and secondary inlets allows control of the total flow through the venturi as well as control of the mix of nitrogen and air exiting the outlet.

Preferably, at least one valve includes:
a control chamber; and
a control member, said control member having a first position within the control chamber and a second position within the control chamber.

Preferably, the first position of the control member corresponds to a first degree of restriction of the control chamber and the second position of the control member relates to a second degree of restriction of the control chamber.

Preferably, a clearance is provided between the control member and the control chamber in the first and second positions whereby each of the first and second degrees of restriction allow some How of gas through the control chamber.

Preferably, one of the first or second degrees of restriction may substantially prevent any flow of gas through the control chamber.

Preferably, the flow control valve includes an actuator for the control member.

Preferably, said actuator is a solanoid.

Preferably, the solanoid is adapted to pulse the control member in the first or second position for a given duration.

Preferably, the solenoid is adapted such that said duration of said pulse(s) can be determined to an accuracy of approximately a millisecond.

Preferably, the apparatus includes a pressurised gas supply connected to the primary inlet.

Preferably, the pressurised gas supply includes at least one pressure regulator.

Preferably, the pressurised gas supply includes at least two pressure regulators.

Preferably, a combination of pressure of the pressurised gas supply connected to the primary input and the dimensions of the venturi is adapted to create a pressure at the secondary inlet that is lower than ambient atmospheric pressure.

Preferably, the pressurised gas supply comprises a supply of inert gas.

Preferably, the pressurised has supply includes a supply of Nitrogen.

Preferably, the supply of Nitrogen comprises a Nitrogen bottle.

Preferably, the supply of nitrogen comprises a nitrogen generator.

Preferably, the secondary inlet is provided with a supply of air.

Preferably, the supply of air comprises ambient atmosphere.

BRIEF DESCRIPTION OF DRAWINGS

Further aspects of the present invention will become apparent from the following description which is given by way of example only and with reference to the accompanying drawings in which:

FIG. 5b shows a mixing head according to the same embodiment as FIG. 5a from an alternative view to FIG. 5a.

DETAILED DESCRIPTION OF THE PREFERRED EMBODIMENT

Figure 1:
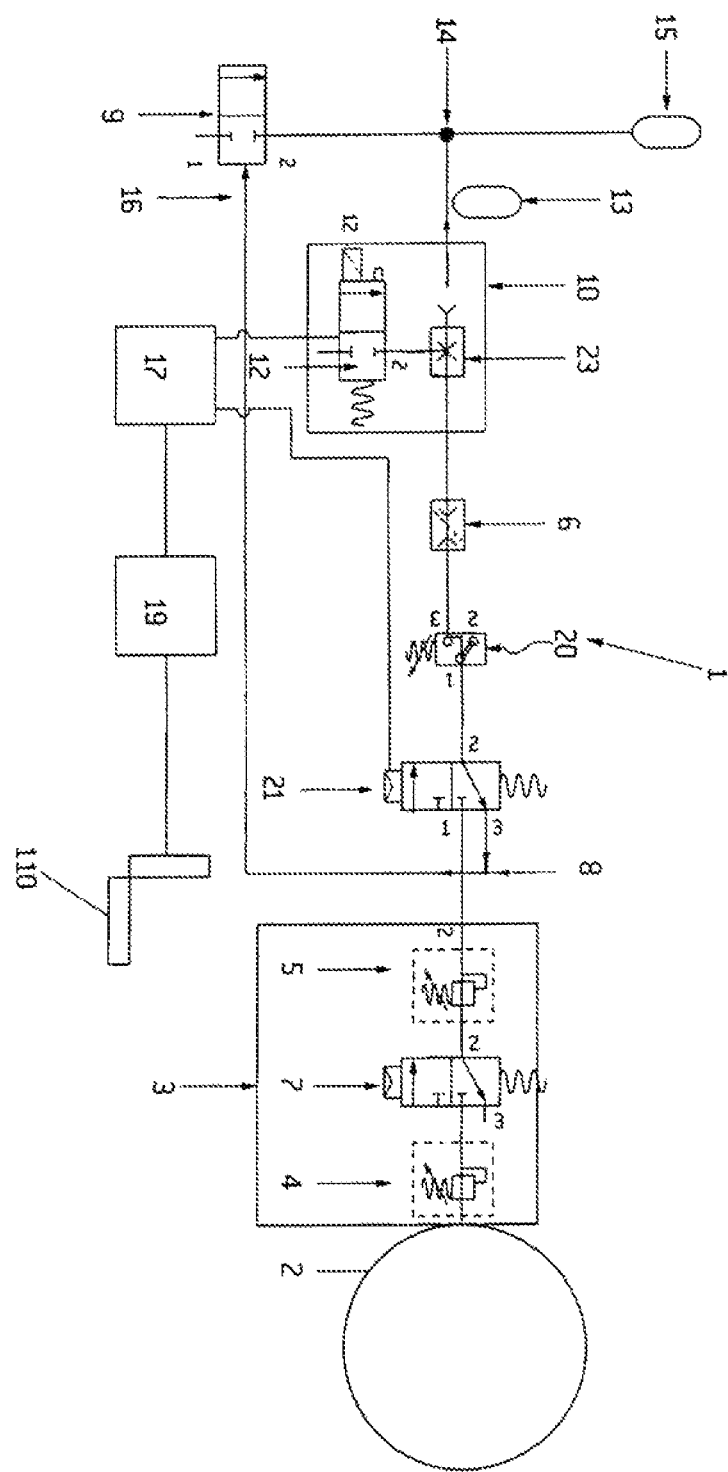
FIG. 1 schematically shows a pneumatic system according to a preferred embodiment of the present invention.

FIG. 1 is a schematic diagram of a circuit 1 (which may also be referred to as a pneumatic circuit or a hypoxic circuit) of a hypoxic training apparatus according to a preferred embodiment of the present invention.

The circuit 1 is supplied with a pressurised fluid, in this case nitrogen gas $N_2$, from the gas cylinder 2.

The gas cylinder 2 feeds a regulator stage 3. This stage may have a pair or series of pressure regulators 4, 5 to regulate, the pressure precisely even over the wide range of pressures of a nitrogen bottle at various stages of fill. Typically, the pressure in a nitrogen bottle may vary from 140 bar (full) to 2 bar (empty). A nitrogen generator could be substituted for the gas cylinder 2.

The regulator stage 3 has an on/off valve 7 which is preferably located between the regulators 4 and 5. The regulator stage 3 feeds a flow valve 6 via on/off valve 21 and pressure switch 20. If a supply stage on/off valve 7 of suitable maximum flow rate is used, the flow valve 6 may possibly be eliminated. The supply stage on/off valve 7 controls whether any nitrogen is supplied to the rest of the system. The components 6, 20, 21, 3 and 2 act as a first supply of the circuit 1 to supply nitrogen to the circuit 1. Items 5, 6, and 7 may be arranged in a different order depending on the componentry used.

An on/off valve 21 is connected between the flow valve 6 and the regulator stage 3. This valve can be pulse width modulated to assist in controlling the flow from the flow valve 6 and to provide another degree of control over the mixer 10.

A pressure switch 20 is also connected between the flow valve 6 and regulator stage 3 to allow the operation of the circuit 1 to be tested.

The regulator stage 3 feeds a junction 8 which taps some of the pressure of the outlet of the regulator stage 3 to a pressure activated control for an alternate gas supply on/off valve 9. An alternative, or second, gas is supplied to the system through the valve 9 which acts as a third supply for the circuit 1. In the preferred embodiment, the second gas is atmospheric, normoxic air taken from the surrounds of the apparatus.

The function of the alternate gas supply on/off valve 9 is described later in this description. This valve 9 is similar to the supply stage on/off valve 7. The valve 9 is closed to the alternate supply when a positive pressure is supplied by the junction 8.

The junction 8 also feeds a mixer 10 via an on/off valve 21, pressure switch 20 and flow valve 6.

The mixer 10 has a venturi 23 which has a primary inlet, an outlet and a restriction, neck or reduced diameter portion between the two. This particular venturi includes a secondary inlet at the neck.

The characteristics of Venturis are well known to those skilled in the art. Essentially, they have a reduced diameter portion which experiences a lower pressure than the pressure of gas at the primary inlet when gas moves through the venturi. According to Bernoulli's equation various ratios of pressure at the neck versus pressure at the primary inlet can be arranged by the choice of the venturi dimensions and flow rate supplied at the inlet.

The venturi dimensions and pressure at the primary inlet of the venturi 23 of the present preferred embodiment are chosen so that the pressure at the secondary inlet is lower than ambient atmospheric pressure. This allows the secondary inlet to draw in atmospheric air in a predetermined ratio to the nitrogen supplied at the primary inlet. The ratio, or mix, of air and nitrogen will be strongly dependent on the ratio of pressures of the nitrogen and the ambient atmospheric pressure. The ratio will also depend on the flow rate allowed to enter the venturi via the primary and secondary inlets.

A valve 12 (e.g., a flow control valve) is included in the secondary inlet to control the flow of gas through the secondary inlet and allow control of the mix of air and nitrogen. The valve 12 controls the airflow of normoxic air from the ambient atmosphere. The valve has two flow states. The valve can pulse for a time in these states or toggle between them.

The valve 12 is provided with a controller 17 which uses a pulse width modulation driver to toggle or pulse between the two flow states of the valve to control the flow through the secondary inlet.

Pulse width modulation allows a two state valve to be used in place of a conventional but more expensive proportional valve. Also, control of the time a valve is open or closed is easier to control or calibrate precisely than control of the size of an aperture in a proportional valve. The time a valve is open or closed will not vary over time and over temperature ranges so mechanical issues affecting precise calibration are avoided. Also, the time precision of a two state valve with a suitable solenoid is in the order of milliseconds.

This allows precise definite settings for the flow rate. For example, if the valve is open 10% of the duty cycle and closed 90% of the duty cycle, the flow rate will be set definitively at a ratio of 1:9 of the two flow states of the valve. This would be difficult to achieve with proportional valves and feedback on the valves state would be required.

Also, the flow rate could be easily adjusted to a ratio of 11:89 with a simple adjustment to the calibration. This also would be difficult to achieve with proportional valves.

The valve 12 may simply be an on/off valve although it is not necessary that one of the flow states is off.

For a given flow through the flow valve 6, the controller 17 can control the mix of first and second gasses in the mixer 10 via the valve 12. If the first gas is nitrogen and the second is air the controller 17 can control the level of oxygen supplied by the mixer 10.

The mixer 10 feeds air of a predetermined mix to a reservoir 13 (e.g., a bag, a bellow, etc.). The bag 13 acts as a reservoir. The reservoir 13 is supplied with the average flow rate of the subject's breathing from the mixer 10. The reservoir 13 feeds an output stage junction 14 which feeds a mask 15 for use by the subject (not shown).

The mask 15 is adapted for a given type of subject, which might typically be a human or a horse. Suitable masks will be apparent to those skilled in the art.

The junction 14 is fed by an alternative supply on/off valve 9 which feeds atmospheric air from a third supply as an alternative to the hypoxic mix from the reservoir. The reservoir 13 typically includes a bellows which might include a breathing bag. As mentioned earlier in this description the alternative supply on/off valve 9 has a control port and closes atmospheric air to the junction 14 when a hypoxic mix is being supplied to the reservoir 13 and junction 14.

If the nitrogen feed to the mixer 10 is shut off, the alternative supply stage valve 9 opens and the mask 15 is fed via the junction 14, by both the bag and the atmosphere simultaneously for a period. This occurs until the reservoir 13, which is no longer being fed by the mixer 10, is depleted. At this point, only atmospheric air is supplied to the mask 15, as an alternative to the hypoxic mix. Before the reservoir 13 is depleted, the mask 15, at the outlet of the circuit, will be supplied air that is a mix of normoxic air, via valve 9, and hypoxic air, from the reservoir 13. This mix starts at 50/50 then gradually becomes fully normoxic as the reservoir 13 is depleted. Alternatives to the ratio of 50/50 can be arranged by the size of the valve 9, and its associated resistance to airflow relative to that of the reservoir 13.

The controller 17 might typically be a micro-controller but other suitable controllers will be known to those skilled in the art. The controller 17 may control a solenoid that drives the value 12. It may do this Via a pulse width modulation driver, amplifier or other suitable means known to those skilled in the art.

Controllers that provide a processor that can carry out the steps herein described will be known to those skilled in the art, and any of these may be incorporated.

The controller 17 receives a pulse oximetry signal from an oximeter 19 (e.g., a pulse oximeter), which measures the blood oxygen calibration, or SPO.sub.2, of the subject (not shown). This oximeter 19 may have an attachment 110 for the ear of the subject, if the subject is human for example. An ear-fitted oximeter allows the subject to carry out a relatively wide range of tasks during hypoxic training. Typing is one example. However, any suitable oximeter known to those skilled in the art can be used to provide the controller 17 with a measurement of SPO.sub.2 or blood oxygen saturation.

The controller 17 monitors the oximeter reading during a training programme. The oximeter indication can be used as feedback for continuous control of the mix of hypoxic air supplied by the mixer 10 or may be used to shut off nitrogen supply to the reservoir 13 and open valve 9 to a normoxic supply when the oximeter indication does not satisfy given conditions. Feedback control typically consists of choosing an oxygen content of hypoxic air that is likely to maintain or restore a given $SPO_2$ level as indicated by the oximeter 19.

A hypoxic training session or programme will typically involve intermittent supply of hypoxic air to the mask 15 with normoxic air supplied via valve 9 in periods between hypoxic supply periods. The preferred programme has 70% of the time of a session as hypoxic and 30% of the time normoxic with the normoxic periods stalling with an even mix of hypoxic and normoxic supplies. As discussed above, the even mix changes gradually to full normoxic as the reservoir 13 is depleted.

The controller 17 may monitor time dependent characteristics of the oximeter indication such as $SPO_2$ maxima and minima rise, fall and settle times of $SPO_2$ levels. The controller may also monitor time dependent characteristics such as whether the $SPO_2$ is tapering off and increasing or decreasing at a changing rate. Here, settle times are the time taken to reach a given $SPO_2$ level. This may be the time taken to fall to a given higher $SPO_2$ or time taken to rise to a given $SPO_2$ from a lower level.

Typically, a programme might consist of 7 to 8 minutes with the hypoxic supply on and 2 to 3 minutes with hypoxic supply off. The mix of air to nitrogen might be constant for the programme and maintained using feedback from the oximeter 19 to be constant over the five minute hypoxic interval.

As discussed in greater detail with reference to FIG. 7, the apparatus may be calibrated occasionally with an oxygen analyser so that the controller will be able to set calibrated mixes of hypoxic air. Typically, the controller will read a stored duty cycle time such as 400 ms and read a portion of the duty cycle for the valve 12 to spend in one of its two states. For example, it may spend 100 ms open every 400 ms. The controller 17 may access this data by reference to a given oxygen content for the hypoxic air. For example, 8% may correspond to a 400 ms duty cycle and 100 ms spent 'open' per data cycle. This allows the controller 17 the option of supplying calibrated mixes of hypoxic air and using the oximeter only in a safety capacity. Various alternative options of control and/or training programmes will be apparent to those skilled in the art and these might include the use of calibrated mixes or real time feedback control from the oximeter 19.

The controller 17 will typically not commence supply of nitrogen to the mixer 10 until it receives an oximeter 19 indication that meets criteria read by the controller 17. This provides a safety feature for use of the apparatus. In this case, a subject would not be supplied hypoxic air until their blood oxygen level had been indicated to ensure that they are in fact wearing the oximeter 19.

The supply of hypoxic air may then be conditional on the subject maintaining a safe blood oxygen level and exhibiting no adverse time dependent blood oxygen level characteristics. This mode of operation would ensure that the hypoxic training apparatus could not be used other than in a safe manner.

The use of feedback from an oximeter 19 attached to the subject eliminates the need for an oxygen analyser to analyse the levels of oxygen in the hypoxic air supplied to the subject. The oxygen analyser would only be used to calibrate the duty cycle and open time for a given oxygen content. This calibration data need only be set occasionally. The use of an oxygen analyser only for calibration allows for significantly more economical construction of the apparatus as an oxygen analyser is generally an expensive piece of equipment it also allows for a more robust compact and portable apparatus.

The use of feedback directly from an oximeter 19 connected to a subject also adds a degree of intrinsic safety to the apparatus over apparatus that only uses feedback from the mix. This facilitates use of the apparatus in unsupervised environments such as in the home.

Additionally, the use of an oximeter 19 to provide feedback to control the circuit 1 allows more precise control of hypoxic training conditions. This is because training creates a given $SPO_2$ level in the subject and it is this condition that creates suitable beneficial stress to the subject. Simply providing a given $O_2$ content in the hypoxic supply will create differing $SPO_2$ levels in different subjects.

Figure 2:
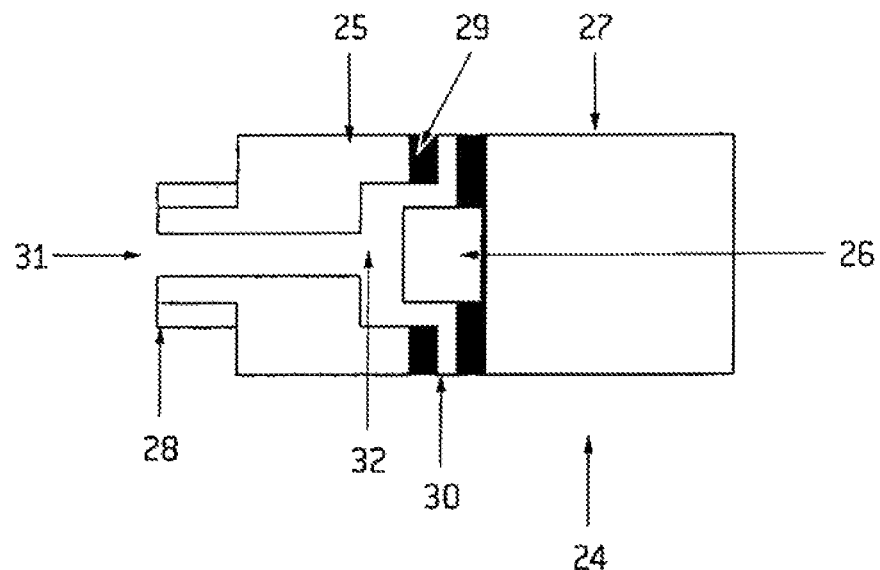
FIG. 2 shows a flow control valve in a relatively closed configuration according to the same embodiment of the present invention as FIG. 1.
Figure 3:
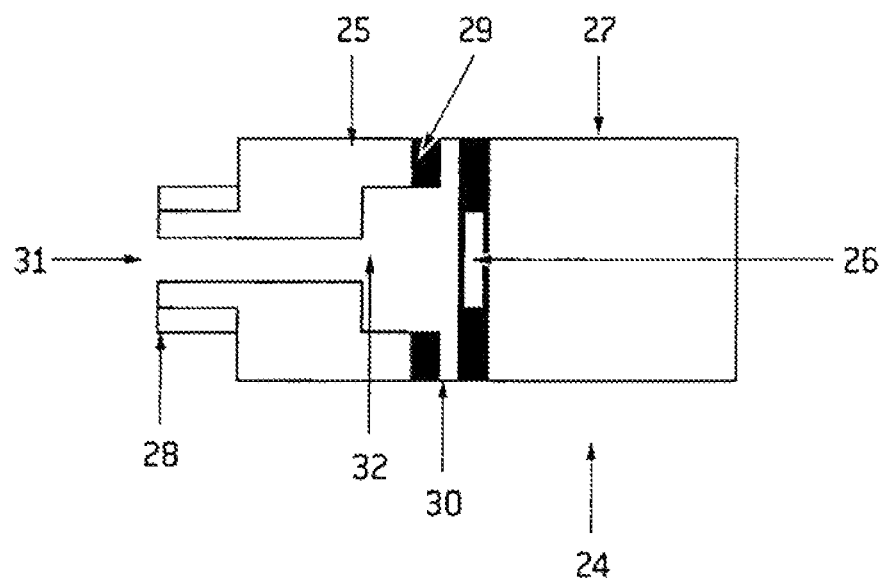
FIG. 3 shows a flow control valve in a relatively open configuration according to the same embodiment of the present invention as FIGS. 1 and 2.

FIGS. 2 and 3 show a valve 24 which may be substituted for the valve 12 in the secondary feed of the mixer 10. The valve 24 has two different flow states, each corresponding to a different ratio of flow. The valve 24 can toggle between these flow states. The valve is used in conjunction with a pulse width modulation controller to control the flow of air into the secondary inlet of a venturi in the mixer 10. The flow rate toggles between two flow states, neither state corresponding to zero flow, to create a given ratio of the two flow states over a given interval. This achieves a rate of flow intermediate to those of the two flow states of the valve.

FIG. 2 shows the valve 24 in a relatively closed configuration in which the flowrate through the valve 24 will be relatively low.

FIG. 3 shows the same valve 24 in a relatively open configuration in which the flowrate through the valve 24 will be relatively high.

The valve 24 has a valve body 25, solenoid bolt 26, and a solenoid 27. The valve body 25 has a threaded end 28 for connection to the secondary inlet of the mixer 10. The valve body 25 and solenoid 27 are separated by a spacer 29, which might be a set of washers or be a drilled hole(s) in the valve of the body. The spacer 29 allows coarse adjustment of how far the solenoid bolt 26 extends into the valve body 25 at maximum extension. The valve body 25 and solenoid 27 may be separated more or less by the choice of spacer 29 to allow coarse adjustment of the restriction of the control passage 32 and thereby coarse adjustment of the restricted flow rate of the valve.

The valve has an inlet passage 30, an outlet passage 31 and a control passage 32. Positioning of the solenoid bolt 26 in an extended position into the valve body 25 and control passage 32 (as shown in FIG. 2) causes a partial restriction of the control passage 32. The partially restricted and unrestricted states of the passage 32 correspond to two different states of flow through the passage 32. This allows the flow of gas through the valve body 25 to be controlled between restricted and unrestricted flow states. When the solenoid bolt 26 is extended, as shown in FIG. 2, a first relatively restricted flow is allowed through the valve body 25. When the solenoid bolt 26 is retracted, as shown in FIG. 3, a second relatively unrestricted flow is allowed through the valve body 25.

The controller 17 controls the solenoid 27 to either retract or extend the solenoid bolt 26 between two extreme positions such as those shown in FIGS. 2 and 3. Flow rates intermediate to the two flow rates can be achieved by pulse width modulation of the solenoid 27. For example, the first rate might relate to a feed for the venturi 23 which achieves the most hypoxic output mix to the mask 15. The second rate might relate to a feed that achieves the least hypoxic mix of the mask 15. Pulse width modulation between the two rates achieves mixes in between these two extremes.

The valve 24 (e.g., a solenoid control valve) is an economical valve for the hypoxic apparatus because it does not need to seal or completely close off gas flow. This means that fractional contact is not needed between parts of the valve. This reduces wear and eliminates the need for any seals between moving parts.

Figure 4A:
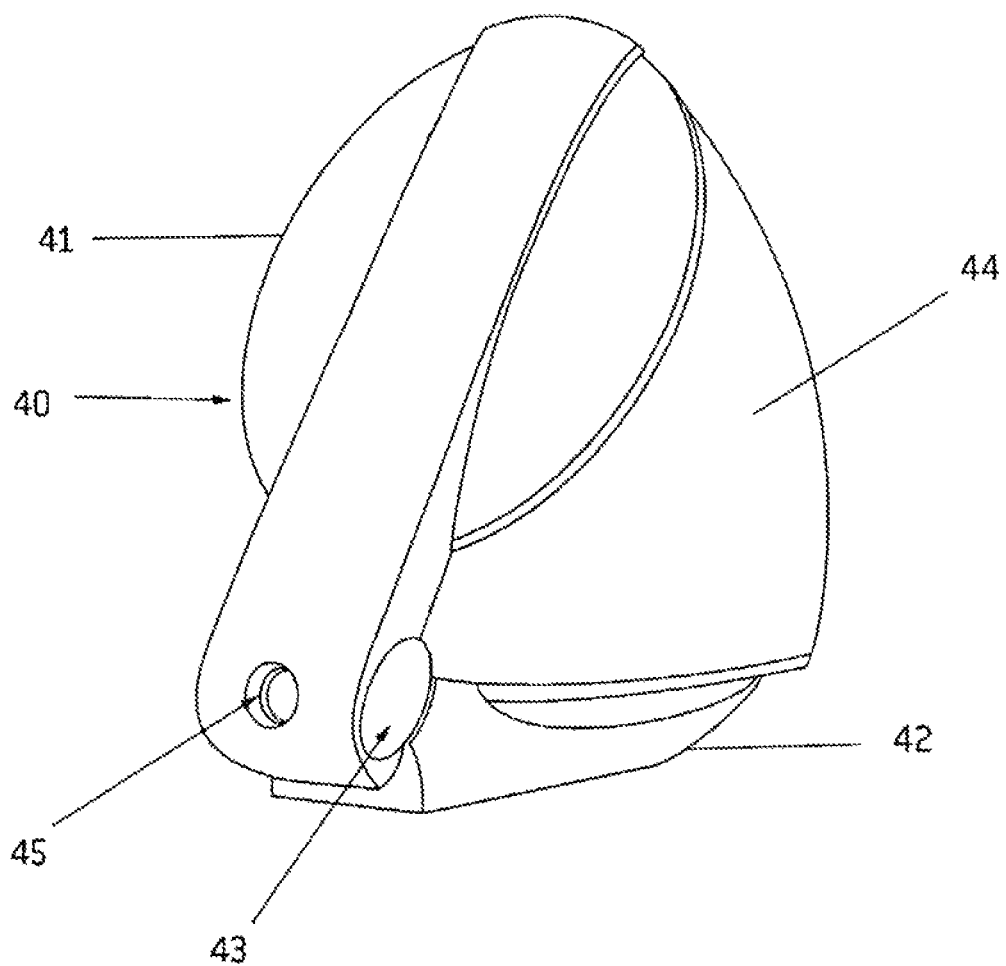
FIG. 4a shows a perspective view of a mixing head of a hypoxic apparatus according to the same embodiment of the present invention as FIGS. 1 to 3, shown in an opened state.
Figure 4B:
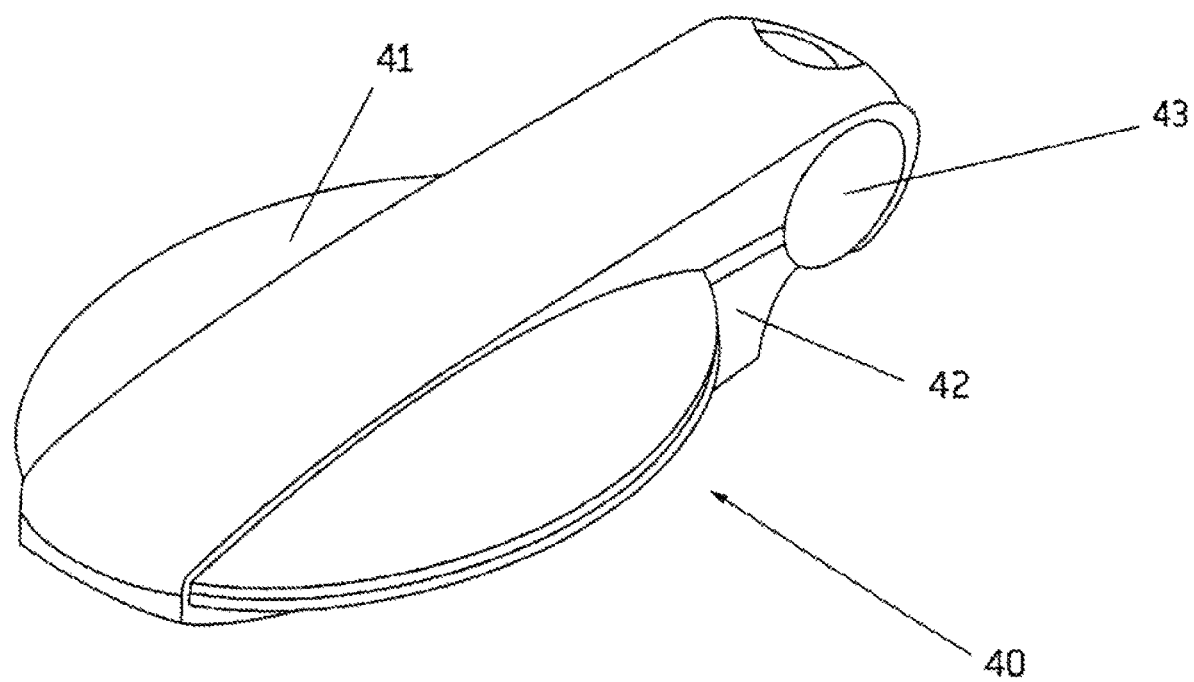
FIG. 4b shows a perspective view of a mixing head for a hypoxic apparatus according to the same preferred embodiment as FIGS. 1 to 4a, shown here in a closed state.

FIGS. 4a and 4b show a mixing head housing 40 forming part of a hypoxic training apparatus according to a preferred embodiment of the present invention. FIG. 4a shows the housing 40 in an open state while FIG. 4b shows the housing 40 in a closed state.

Referring to FIG. 4a, the housing 40 is formed from a first, or upper, member 41 and a second, or lower, member 42 connected at a hinge 43. Typically the hinge 43 is formed from interlocking hinge portions of the upper member 41 and lower member 42.

The housing 40 has a bellows 44 connected between the upper member 41 and lower member 42. The upper member 41 and lower member 42 provide a mounting for the upper end and lower end, respectively, of the bellows 44. The term 'bellows' is intended to encompass any flexible container which can deform to accommodate various volumes of gas. The bellows shown in FIG. 4a is formed by a flexible wall connected between, and at the periphery of the circumference of, the upper member 41 and lower member 42. The bellows can deform by either inward movement of the walls or by relative movement of the upper member 41 and lower member 42. The suitability of either approach for specific applications of the invention will be apparent to those skilled in the art. The upper member 41 and lower member 42 may hinge inwards towards each other to deflate the bellows 44.

The housing 40 has a gas supply aperture 45 formed in the upper member 41 on the interlocking portion which forms part of the hinge 43. A corresponding gas outlet aperture (not shown) is formed in the corresponding portion of the lower member 42. The gas supply aperture 45 on the upper portion and the corresponding aperture (not shown) formed in the lower member 42 is arranged so that they are aligned only when the upper member 41 and lower member 42 are in an open configuration. This alignment of the apertures, prevents dust or contaminants entering the supply for the bellows 44 when not in use and provides a gas supply outlet when the mixing head is in use.

FIG. 4b shows the mixing head with the upper member 41 and lower member 42 in a closed configuration. In this view, the bellows 44 is not visible as it is enclosed entirely within the closed housing formed by the upper member 41 and the lower member 42.

Figure 5A:
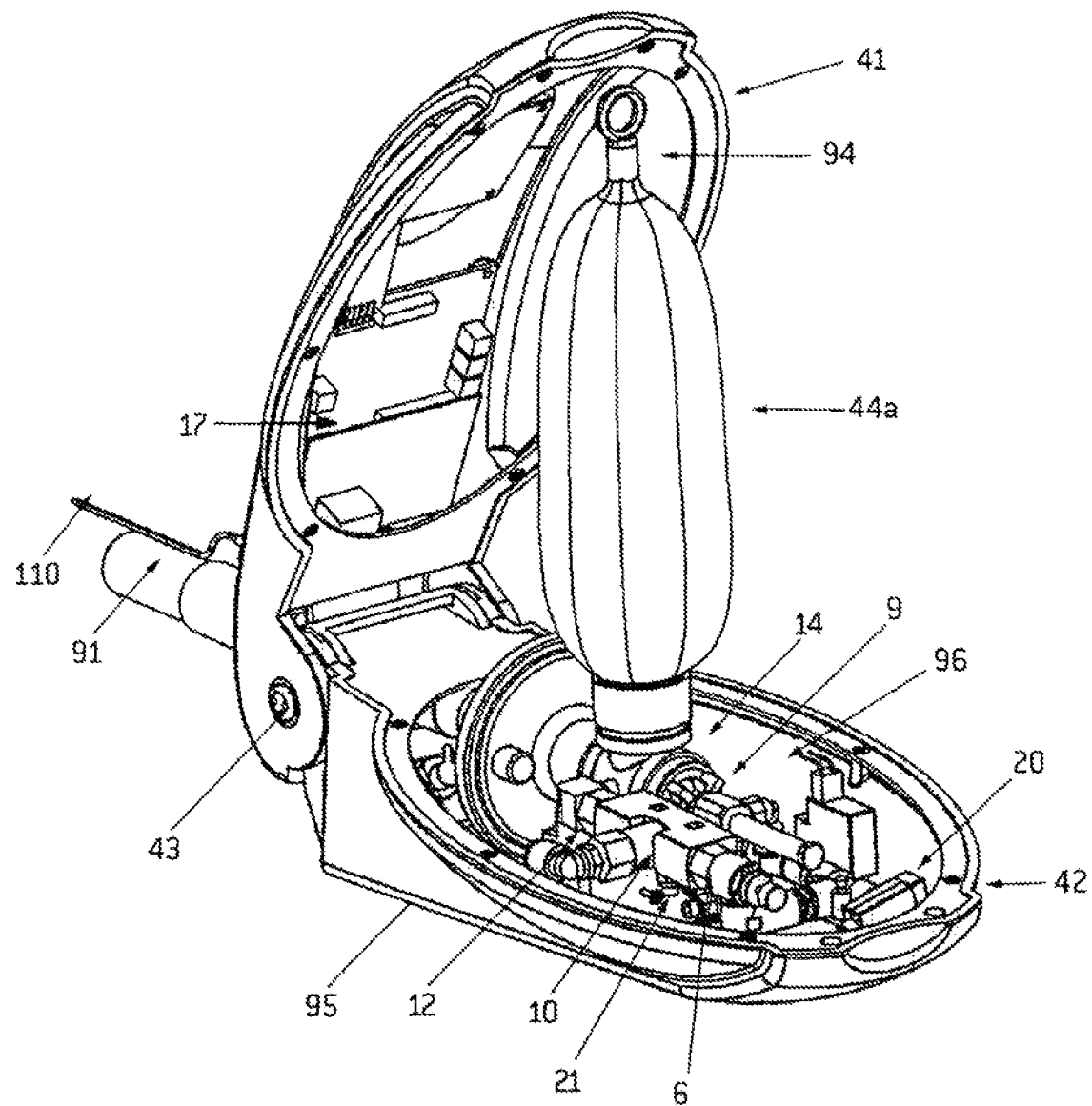
FIG. 5a shows a perspective view of a mixing head according to an alternative embodiment as FIGS. 4a and 4b in which the internal components are shown.

FIG. 5a shows a perspective view of an alternative embodiment to FIGS. 4a and 4b of the mixing head. In this embodiment the bellows 44 comprises a breathing bag 44a rather than a flexible wall connected between the upper member 41 and lower member 42. It will be appreciated by those skilled in the art that they container may be complete flexible (as in the bag 44a depicted in FIGS. 5a and 5b), or partially flexible, or partially rigid (as in the configuration depleted in FIGS. 5a and 5 in which the internal area of the bellows is formed from the bag 44a and the upper 41 and lower 42 members of the housing 40) and variations thereof. Here parts have been removed to reveal internal components. FIG. 5a shows the upper member 41 and the lower member 42 pivotally connected at a hinge 43. The lower member 42 has a flat base 95 formed thereon. The flat base 95 allows the lower member 42 to rest in a stable manner on a flat surface (not shown).

The lower member 42 also has an internal aperture 96 formed therein to allow parts of pneumatic components to project out of the lower member and through a corresponding internal aperture 94 formed in the upper member 41 when these members 41 and 42 are in a closed configuration.

Figure 5B:
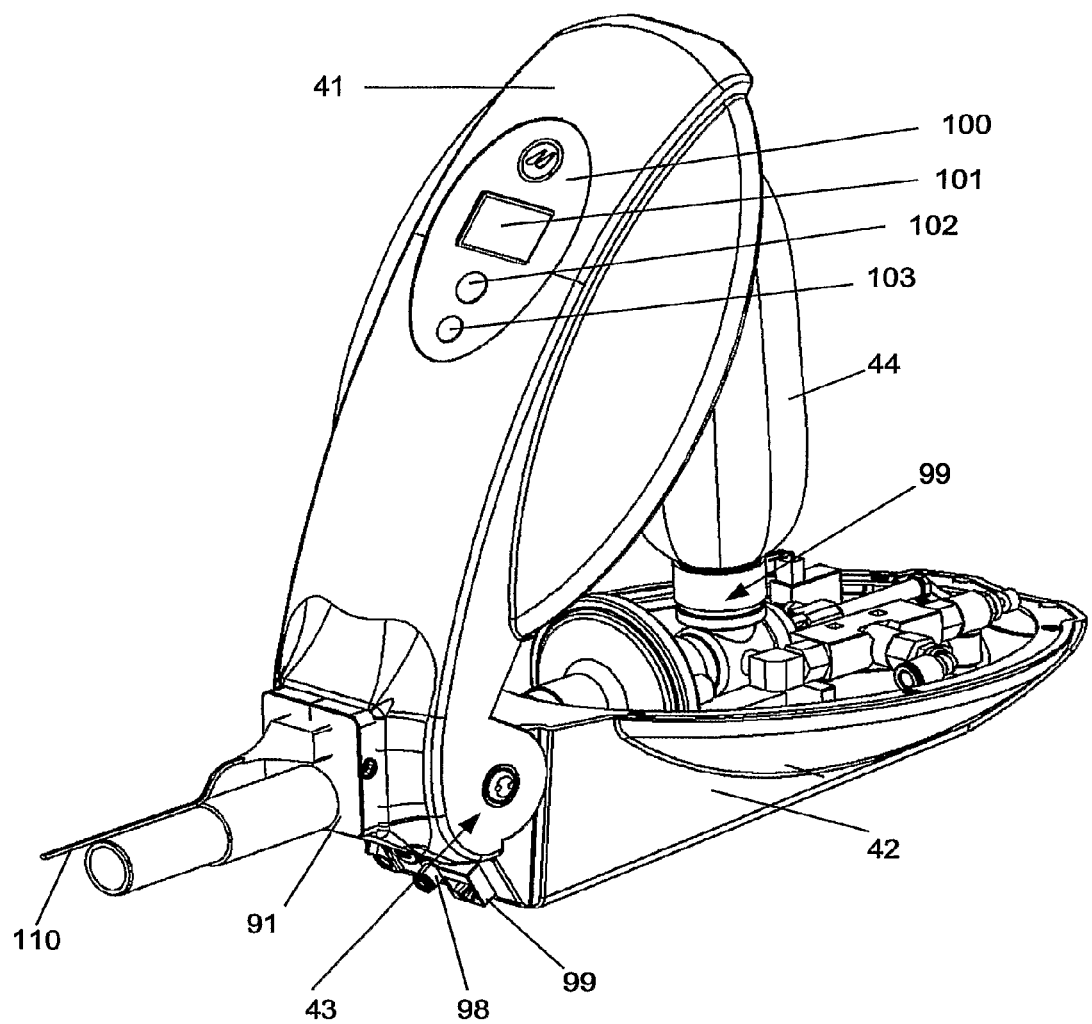

FIG. 5b also shows the bellows 44 formed in part by a breathing bag 44a which provides the reservoir 13 of the circuit 1. The breathing bag 44a is shown attached to the pneumatic components in the lower member 42. An opposite end is shown attached to the upper member 41, although FIG. 5a does not show the connection point. This configuration of the breathing bag 44a is upside-down compared to conventional use of a breathing bag. However, this unconventional arrangement allows connection of the breathing bag 44a to pneumatic components housed in the lower member 42. Housing these components in the lower member 42 allows their weight, relative to electronic components, to act to stabilise the housing 40 when in an open configuration.

The dimensions of the upper member 41 and lower member 42 and the location of the connection point (not shown) of the opposite end of the breathing bag 44a to a pneumatic circuit are chosen to provide optimal extension of the breathing bag 44a for it to operate in an upside down configuration. In this optimal extension the pneumatic circuitry does not have to work to lift or stretch the bag while partially filling or emptying it.

The pneumatic circuitry housed the lower member 42 includes a valve 12 connected to a mixer 10. The mixer 10 is also connected to a second control valve 21 which is connected to flow control valve 6. The mixer is connected to a junction 14. Also connected to the junction 14, in parallel, is an on/off valve 9. A pressure switch 20 is also shown housed in the lower member 42.

The electronic component including the controller 17 is shown housed in the upper member 41. The relatively light weight of electronic componentry, and the fact that the upper member 41 is substantially hollow, means that the upper member 41 does not destabilise the device even when in an open configuration.

FIG. 5b shows an alternative perspective view to FIG. 5a. Visible in FIG. 5b, but not in 5a, is an entry point 98 for a supply of nitrogen, and an electronic connection 99, which might be an interact port or a craft port.

FIG. 5b shows a connector 91 for a gas supply hose for a mask 99 (not shown in this figure). The connector 91 connects to a gas supply outlet formed by the aperture 45 in the upper member and the corresponding aperture (not shown) in the lower member 42 when these apertures are aligned. The connector 91 incorporates a connection for a pulse oximetry sensor 19 via the attachment 110.

FIG. 5b also shows a user interface 100 which includes an LCD screen 101 and two buttons 102 and 103. This interface 100 allows the subject (not shown) to carry out basic control operations such as selecting their program, stopping and starting the program and pausing the program.

Figure 6:
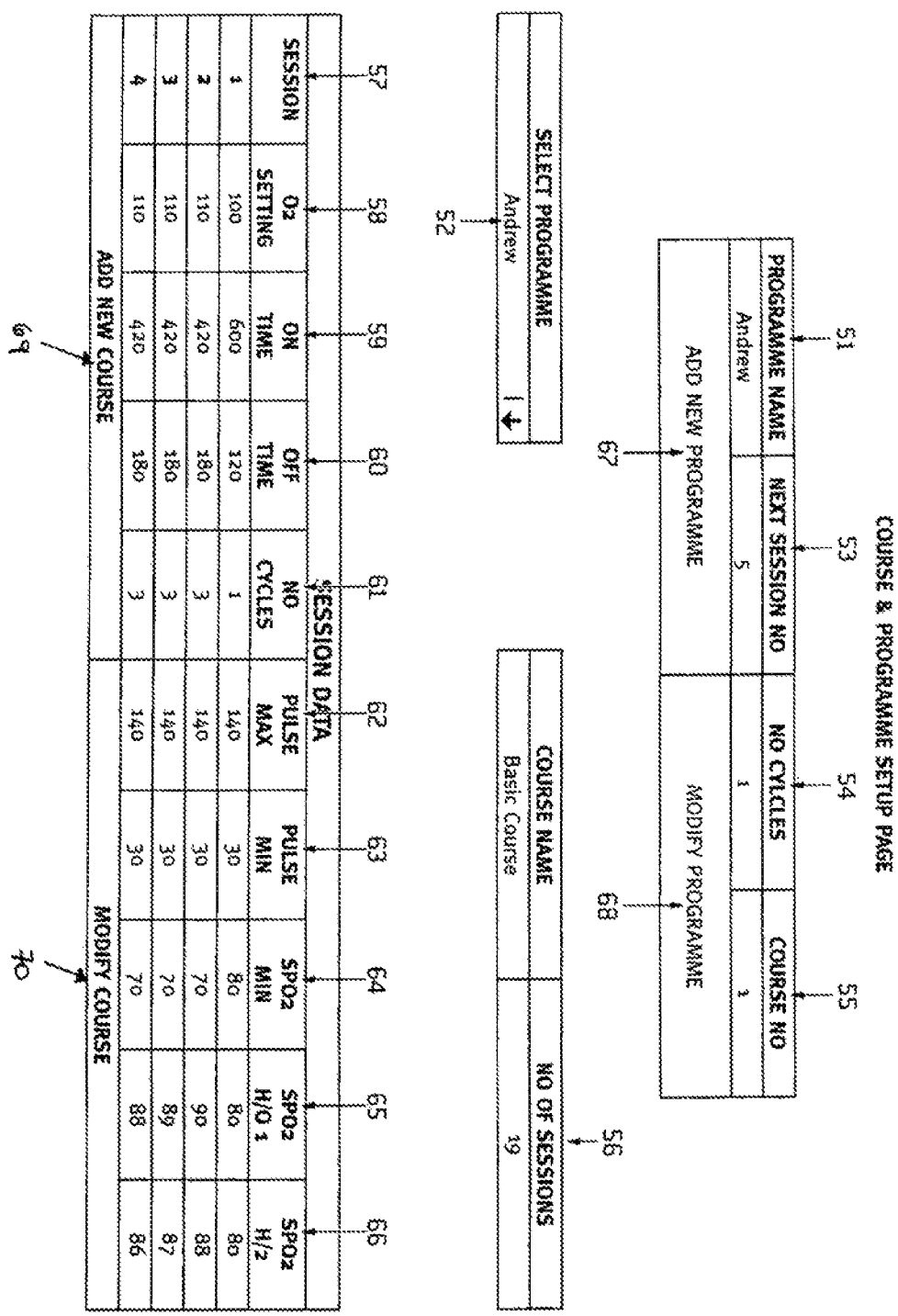
FIG. 6 shows a screen provided by an interface of a hypoxic apparatus according to a preferred embodiment of the present invention, this screen relating to training courses and programmes.

FIG. 6 shows a screen of an internet protocol graphical user interface (GUI) provided by a preferred embodiment of the hypoxic training apparatus. The interface is provided by the apparatus in a format that is viewable with an internet browser. This means that any browser enabled computer can interface with the apparatus without requiring any apparatus specific software to be installed.

The screen shown in FIG. 1 has an identifier for the subject in field 51. It also has an identifier for a particular program assigned to the subject in field 52. Field 52 is a control that allows the particular program to be chosen.

The screen shown in FIG. 6 has an identifier for the training subject in field 51. It also has an identifier for a particular training session programme assigned to the subject in field 52. Field 52 is a control that allows a particular session or programme to be chosen.

Field 53 indicates the number of the next training session. Field 54 indicates the number of times a training session will cycle through hypoxic and normoxic supplies. Field 55 indicates the type of programme of training sessions that will be administered. This is indicated by a number or a name, such as 'Basic Course'.

The lower part of the screen shows a table which sets out the parameters that define a training session.

The first column 57 of the table 56 shows a session number.

The second column 58 shows an $O_2$ setting which indicates an oxygen content to be selected by default for the training session.

The third column 59 shows the period of hypoxic supply in seconds.

The fourth column 60 shows the period in seconds when hypoxic supply to the reservoir 13 or bellows 44 is turned off and the valve 9 is opened to the normoxic atmosphere.

The fifth column 61 shows the number of times a hypoxic/normoxic cycle will be repeated.

The sixth column 62 shows the maximum allowable pulse rate as indicated by a pulse oximeter. The apparatus may suspend supply of hypoxic air if this is exceeded.

The seventh column 63 shows the minimum acceptable pulse, rate, or heartbeat rate, below which supply of hypoxic air may be exceeded.

The eighth column 64 shows a preset level of $SPO_2$. This preset might be referred to as $SPO_2$ Min. This is the suspension minimum $SPO_2$ level. When an $SPO_2$ that is below the suspension minimum is detected, the hypoxic supply will be suspended. This embodiment will store how many times this occurs and will monitor how long a subject has been below the suspension minimum. If, for example it occurs 2 times this embodiment may cancel the training session. Also, some embodiments may store this parameter as part of a training session data set which is read by the controller 17.

The ninth column 65 shows a second preset $SPO_2$ level, referred to as $SPO_2$ H/01. This is the target training $SPO_2$ level. In this embodiment the programme will enable a hypoxic/normoxic mix for a period of 5 seconds when an $SPO_2$ lower than shown in column 65 is observed. This embodiment will also store data indicating when this has occurred.

The tenth column 66 shows a third preset $SPO_2$ level, referred to as $SPO_2$ H/02. This is the resumption minimum $SPO_2$ level. In this embodiment once interrupted, the hypoxic air supply will not be resumed until the $SPO_2$ of column 66 is observed. Meanwhile, normoxic air will be supplied.

Other embodiments may have an initiation minimum $SPO_2$ (not shown) level below which a training session will not be initiated. Other embodiments may also have a minimum suspension interval defining the minimum interval supply of hypoxic air is suspended in any given instance.

The screen also includes buttons 67 to 70 which allow modification of sessions and courses. Here a programme is simply a set of courses common to a subject. The programme might be designated by the subject's name or code unique to the subject. Hence a course is defined by the data in boxes and columns 57 to 66.

As will be understood by those skilled in the art the screen depicted in FIG. 6 and the data described with reference to it is read from a data store associated with the apparatus and the same data store, or an equivalent, is read by the controller 17 to affect the functionality defined by this data.

Figure 7:
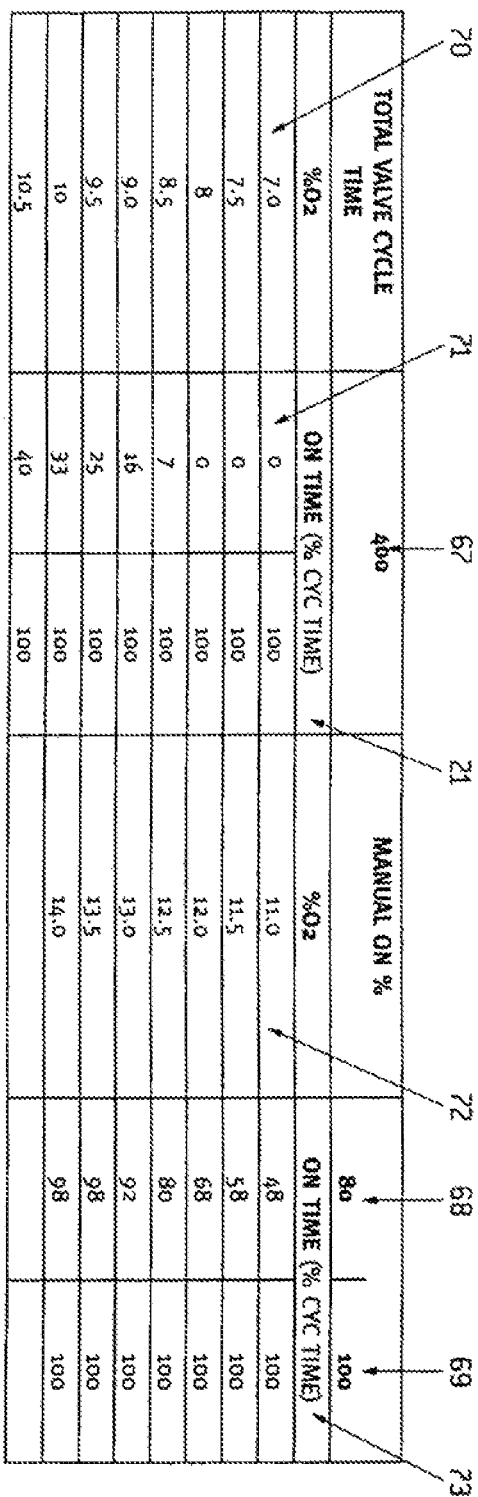
FIG. 7 shows an alternative screen provided by an interface of a hypoxic training apparatus according to the same preferred embodiment as FIG. 6, this screen relating to calibration.

FIG. 7 shows another screen of the internet protocol graphical user interface (GUI) provided by a preferred embodiment of the hypoxic training apparatus. This screen illustrates calibration of the circuit 1 with pulse width modulation of valves 12 and 21. These valves are pulse width modulated to control flow into the venturi 23. The flow of nitrogen through valve 21 and normoxic air through valve 12 determines the mix of oxygen in air exiting the venturi 23. It will be apparent to those skilled in the art that if a valve 21 is pulse width modulated then flow valve 6 may possibly be omitted.

Alternative embodiments of the apparatus may replace the GUIs with a coded file sent over an electronic interface such as the internet or a craft interface or other interfaces known in the art.

Calibration of the circuit 1 will now be described with reference to FIG. 7 and the functionality of the on/off valves being used for both valves 12 and 21.

In the preferred embodiment, the valve 21 supplies nitrogen to the primary inlet of the venturi 23. The valve 12 supplies normoxic air into the secondary inlet at the neck of the venturi 23. In the preferred embodiment valve 12 is the valve described with reference to FIGS. 2 and 3. However, the valve 12 may be an on/off valve (not shown).

Box 67 sets the period Pulse Width Modulation (PWM) duty cycle in milliseconds. Both valves, 12 and 21, will be pulse width modulated using the same duty cycle period.

Box 68 sets the percentage time of the PWM duty cycle period for which valve 12 will be open. In FIG. 7 the value 80 denotes that of the 400 ms PWM period, the valve 12 will be open for 80% of the time, or 320 ms.

Box 69 is similar to box 68 except that it relates to valve 21.

Boxes 68 and 69 are GUI inputs which allow an operator to set calibration data for a given oxygen content for the output of the circuit 1. This calibration would be carried out using an oxygen analyser to monitor the oxygen content of air supplied by the circuit 1. Adjusting one or both of the boxes 68 and 69 would adjust the oxygen content (% $O_2$).

It will be appreciated that the oxygen content can be adjusted with adjustments to only valve 12. However, the preferred embodiment of the present invention has a valve 21 to allow not only the oxygen content but the total volume of air supplied by circuit 1. This is advantageous in preventing a subject from maintaining high $SPO_2$ levels by breathing relatively more air to compensate for a lower oxygen content.

Columns 70 to 73 represent a lookup table used by the controller 17 of the circuit 1. In operation, the controller 17 looks up, or reads, the valve pulse times in columns 71 or 73 that relate to a given $O_2$ content in columns 70 or 72. In some embodiments the controller 17 may adjust the selection of $O_2$ content so as to attempt to maintain a given $SPO_2$ level. Here the controller 17 uses the $SPO_2$ level as feedback to control the $SPO_2$ level of a training subject.

The values in columns 70 and 72 are the oxygen contents required by a coarse. The values in columns 71 and 73 are the percentage open times of the PWM cycles for valves 12 and 21. Typically, the operator who is calibrating the circuit 1 will find the values for columns 71 and 73 by adjusting boxes 68 and 69 while observing an oxygen analyser. Also, typically, but not necessarily, the operator will choose values for columns 71 and 73 that achieve the different oxygen contents in columns 70 and 72 for the same, given total flow rate. This flow rate might be 15 to 16 litres per minute for a human subject.

Figure 8:
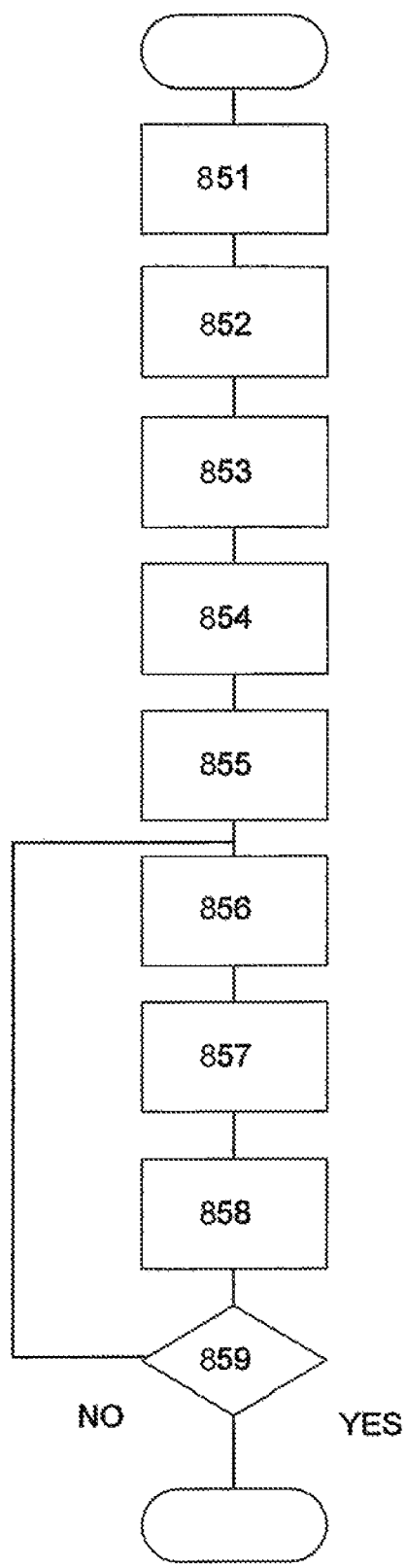
FIG. 8 shows a process carried out by hypoxic apparatus according to a preferred embodiment of the present invention.

FIG. 8 illustrates an algorithm carried out by the hypoxic training apparatus according to a preferred embodiment.

Box 851 denotes a step in which the apparatus receives programme or session data for a subject. It receives this via an internet protocol interface (not shown) provided by the apparatus.

At box 852 a user identifies themselves to the apparatus. This may be done by way of an electronic card, although suitable alternatives will be known to those skilled in the art.

At box 853 a memory store is accessed for details on the users programme or course and pre-training checks are carried out according to the information in the memory store. This information includes data entered into the memory at box 851 but also includes data recorded by the apparatus during previous training sessions. This data includes the time elapsed since the user's last session and also the times the oximetry level of the subject falls below a given preset, such as that shown in FIG. 6, column 64. Various other suitable pre-training checks against corresponding stored information will be apparent to those skilled in the art.

At box 854 a system check is carried out. This involves testing that a reasonable SPO.sub.2 observed. It also involves testing the circuit 1 shown in FIG. 1 by activating various valves, such as valve 7, and monitoring pressure switches such as pressure switch 20.

At box 855 an oximetry test is carried out. This oximetry testing supplies the subject with hypoxic air of a given oxygen level and monitoring their SPO.sub.2 level, and measuring the interval taken for the SPO.sub.2 level to reach a given preset, such as 90% for example. This measurement can be used to assist in characterising the subject's response to hypoxic training. This may be used to select an oxygen content to use initially for a training session.

At box 855 the oxygen content of the hypoxic air supply to a person may be adjusted. The adjustment is made according to information in the memory store and also to the measurement taken at box 854.

In a preferred embodiment, programmes include parameters that determine whether the oxygen levels should be adjusted at all, during a training session under what conditions it should be adjusted and by how much it should be adjusted. For example, a programme assigned to an athlete may specify that the oxygen level in the hypoxic air supplied to the subject should be decreased if the oximetry level measured in the subject does not fall to 90% in a given time interval. A programme assigned to someone with a cardio disorder may specify that a given oxygen level is used for all sessions irrespective of any favourable characteristics observed by the apparatus during training sessions.

At box 856 the hypoxic training session commences with hypoxic air being supplied while the oximetry level of the subject is monitored. This interval is specified in FIG. 2, at column 59, If the first pulse oximetry level present corresponding to a suspension minimum oximetry level is reached, the hypoxic supply to the reservoir 13, shown in FIG. 1, will be suspended until either a time interval has expired or a second resumption minimum oximetry level is observed. This operation is described with reference to FIGS. 11 and 12 below. Interrupting the hypoxic supply will cause the subject to be supplied initially with a mix of hypoxic air from the reservoir 13 and normoxic air from the ambient atmosphere, through valve 9. If the resumption minimum oximetry level is not reached in a given interval the controller 17 may, in some embodiments, select a higher oxygen content.

As the reservoir 13 is gradually depleted, the mix becomes gradually more normoxic. This gradual replacement of hypoxic with normoxic air has been found to avoid the oximetry level monitored in the subject 'bouncing' high when the hypoxic supply is interrupted and replaced with a normoxic supply.

At box 857 the hypoxic supply is assessed for an interval indicated in FIG. 6, column 60. This allows the subject to recover. In the preferred embodiment the hypoxic interval applied in box 856 is approximately 70% of a hypoxic/normoxic cycle in the preferred embodiment also, the normoxic interval, specified in box 57 of FIG. 6, is approximately 30% of the hypoxic/normoxic cycle.

At box 858 the subject's oximetry level is monitored while they are supplied, normoxic air and time dependent aspects are observed. The rise time, fall time taken to reach a given level or other metrics known to those skilled in the art can be used as a basis for the controller 17 selecting a new oxygen content. The rise time, in particular, may also be used to indicate the subjects response to performance under treatment. This indication may be displayed to the subject.

At box 59, the number of hypoxic/normoxic cycles is repeated until the maximum number specified in FIG. 6, column 61 is reached.

Figure 9:
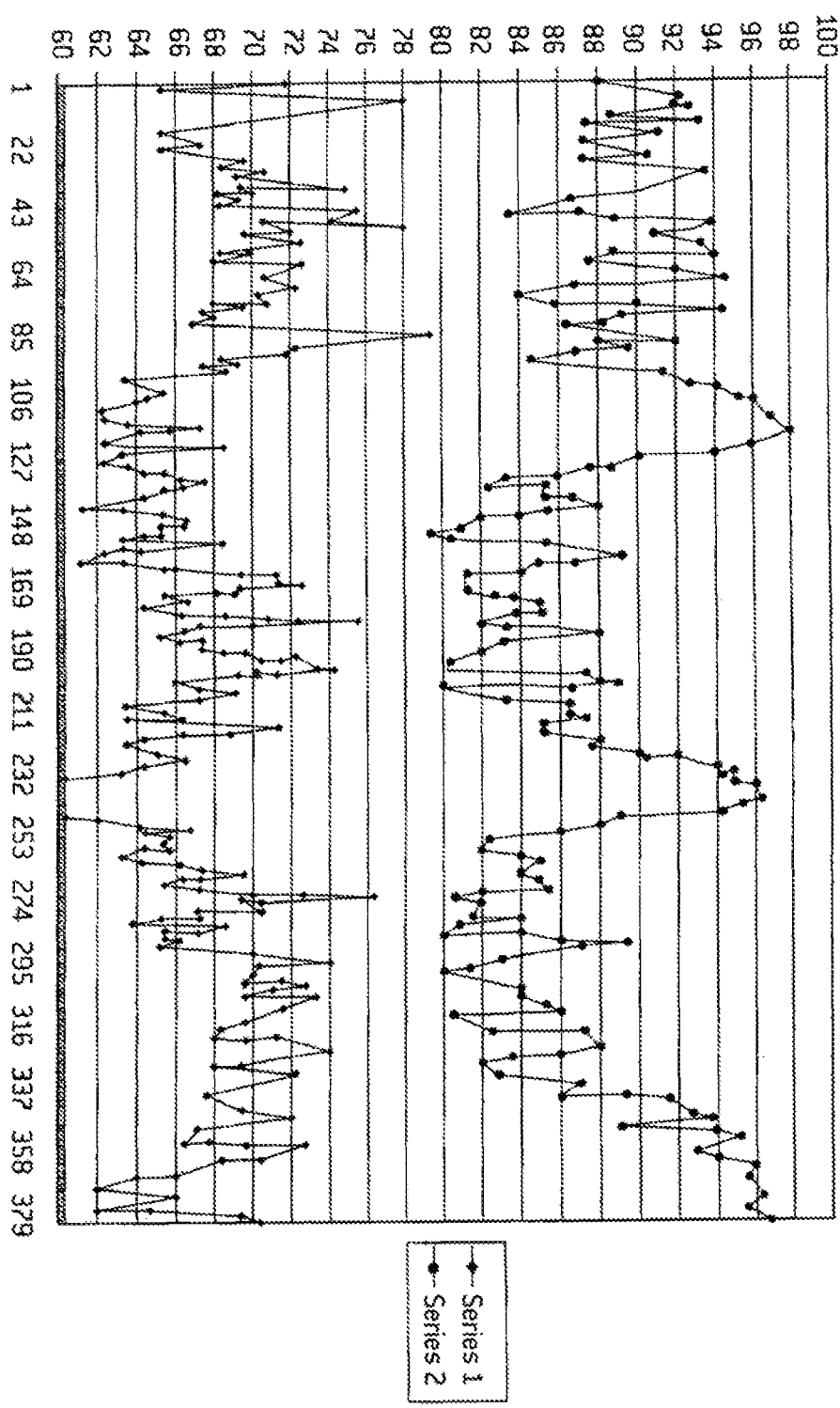
FIG. 9 shows heart beat rates and blood oxygen saturation levels during an example hypoxic training session conducted according to a preferred embodiment of the present invention.

FIG. 9 shows an example of the heart beat rates and $SPO_2$ levels indicated by a pulse oximeter that is monitored by the controller 17. The upper curve shows $SPO_2$ level in percentages. The lower curve shows heart rates in beats per minute.

FIG. 9 shows intervals of lower $SPO_2$ level corresponding approximately to intervals when hypoxic air is supplied to a subject.

FIG. 9 also shows intervals of higher $SPO_2$ levels corresponding approximately to intervals of the hypoxic air supply being interrupted.

Figure 10:
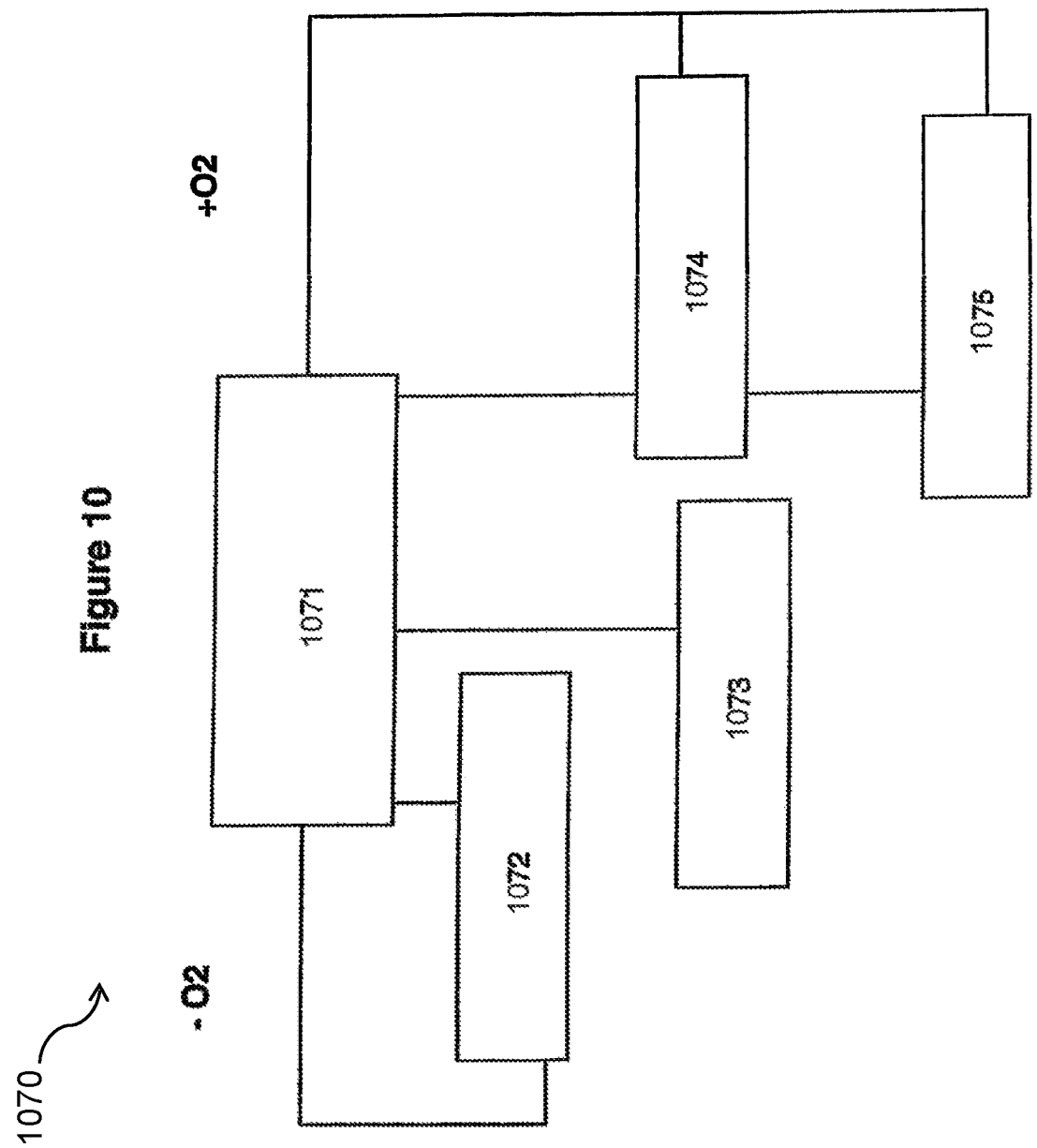
FIG. 10 depicts a process carried out by the controller of a hypoxic apparatus according to a preferred embodiment.

FIG. 10 shows process 1070 carried out by the controller 17 to control the oxygen content in hypoxic air supplied to the subject. This occurs during boxes 856 to 859 as shown in FIG. 8. The process 1070 involves adjusting a selection of the oxygen content in response to a pulse oximetry signal received by the controller 17 from the pulse oximeter 19. Box 1071 depicts the controller 17 monitoring the pulse oximetry signal.

Box 1072 depicts the controller determining that a first predetermined level, referred to as set point 1, and may be $SPO_2$ H/0.1+3 has not been reached within a predetermined interval. Typically this interval is 80 seconds. This condition prompts the controller 17 to adjust the oxygen content downwards. Typically a downward adjustment of 0.5% oxygen content would be made. The sub-process depicted by box 1072 would be repeat so that another downward adjustment of 0.5% would be made if the first set point wasn't reached in another 80 seconds. By this sub-process the oxygen content is adapted to the response of the subject to hypoxic air. This means that subjects with widely differing responses to hypoxic air will experience similar $SPO_2$ levels and thereby receive similar levels of beneficial stress from hypoxic training.

Box 1073 depicts the controller determining that the first predetermined level, set point 1 has been reached that a second set point level, set point 2, has not been reached within a second predetermined interval. Set point 2 may be $SPO_2$ H/0.1 in the preferred embodiment the valve 9 is opened for a short interval, 5 seconds for example. This causes the apparatus to supply a mix of the hypoxic air from the reservoir 13 and normoxic air via the valve 9.

Box 1074 depicts the controller determining that the first and second predetermined levels, set points 1 and 2, have been reached within a predetermined interval. This may indicate that the subject is too responsive to the hypoxic stress provided by the oxygen content. This condition prompts the controller to adjust the oxygen content upwards. Typically an upward adjustment of 0.5% increase would be made. Additionally, the valve 9 may be opened to allow the subjects $SPO_2$ level to be restored to the first predetermined level, set point 1.

Box 1075 depicts the controller monitoring the rate of change of the pulse oximetry level after a given interval. An interval of 10 seconds might be used. If the rate of decline, for example, of the pulse oximetry level is not approaching zero or a positive rate of decline, the controller is prompted to adjust the oxygen content upwards by 0.5% and to open the valve 9 for a predetermined interval of, typically, .delta. seconds.

Figure 11:
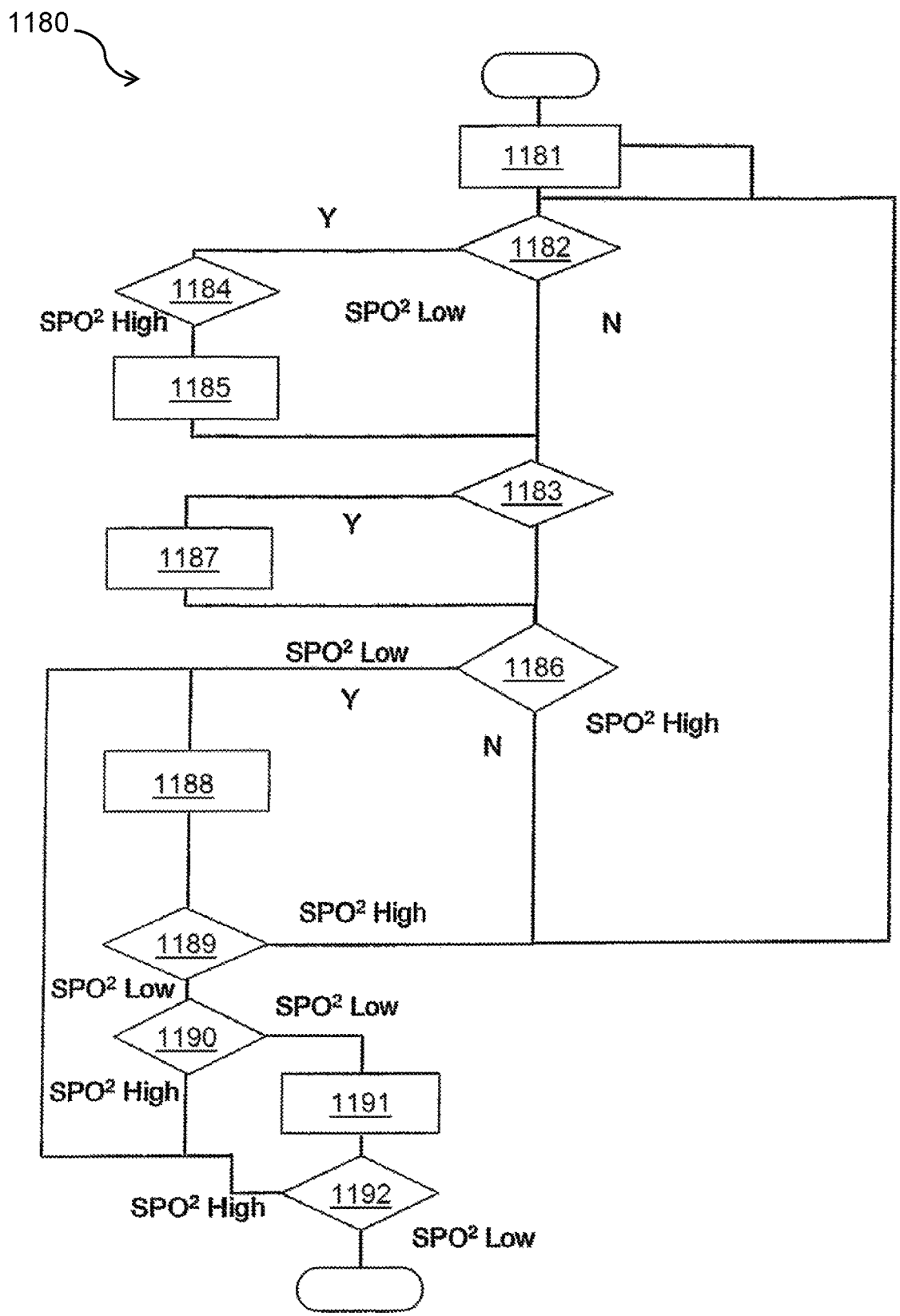
FIG. 11 depicts a process carried out by the controller of a hypoxic training apparatus according to an alternative embodiment, of the present invention to FIG. 10, the process controls a normoxic/hypoxic valve and the selection of oxygen contents during intervals of hypoxic air supply.

FIG. 11 depicts an alternative algorithm to FIG. 10 carried out by the controller 17 (depicted in FIG. 1) of a hypoxic training apparatus according to an alternative embodiment of the present invention. This particular algorithm is carried out during intervals when a stored training session dictates that hypoxic air is to be supplied to a subject.

The algorithm depicted in FIG. 11 controls the circuit 1 (depicted in FIG. 1) to attempt to hold the subject's $SPO^2$ level at an optimal level for hypoxic training. This optimal level is being put in the form of a set of $SPO^2$ presets which are typically stored on the controller 17. Some of these presets are shown in FIG. 6 at columns 64 to 66. These presets are $SPO^2$ min 64, ($SPO^2$H/01) 65, $SPO^2$ H/02. Other presets will be provided by offsets from H/01, in particular. Typically, the additional preset of $SPO^2$ H/01+3 will be provided by adding the value of 3 to the $SPO^2$ H/01 preset. Also typically, a preset of $SPO^2$ H/01−1 will be provided by subtracting the value of 1 from $SPO^2$ H/01. Various values for presets will be apparent to those skilled in the art. However, the control algorithm according to the present invention allows relatively fine control of $SPO^2$ levels in the subject and these allow relatively low $SPO^2$ presets to be set. These low presets provide improved effectiveness of hypoxic training sessions.

The algorithm 1180 begins with box 1181 representing the apparatus supplying hypoxic air of a given starting oxygen content. The oxygen content setting would typically correspond to one of the values shown in column 70 or 72 of FIG. 7. Typically an oxygen content of 10% would be used. At box 1182 the control circuit determines whether a predetermined time interval has elapsed. This time interval is typically 80 seconds. If the time interval has not elapsed, the algorithm moves onto box 1183. If the predetermined time interval has elapsed the algorithm moves onto box 1184 where the $SPO^2$ level of the subject, as measured by a pulse oximeter, is compared to the set point H/01+3. Looking at the example represented by session 1 of FIG. 6 H/01+3 would be 80+3=83%. If the SPO2 level is lower than H/01+3, the algorithm judges that the subject is showing sufficient response to the hypoxic stress and the algorithm continues onto box 1183. If, however, the SPO2 level is not below H/01+3 the algorithm moves to box 1185 at which the oxygen content of hypoxic air supplied to the subject, is reduced by half a percent. Reducing oxygen content will involve selecting anew oxygen content, such as 9.5% for example. This will correspond in the table shown in FIG. 7 to new 'on times' which are applied to a pulse width modulation signal supplied by the controller, or an associated pulse width modulated driver to a solenoid associated with valve 12 of the circuit 1.

At box 1183, the algorithm determines whether the $SPO^2$ level is less than H/01. If this is not the case the algorithm proceeds to box 1186. If the $SPO^2$ level detected is determined to be lower man H/01 the algorithm moves to box 1187 where the hypoxic/normoxic valve, as represented by valve 9, in the circuit 1 is opened for 5 seconds. This causes the subject to be supplied with a mix of hypoxic and normoxic air initially. This mix becomes normoxic as the subject depletes the reservoir 13 (as shown in FIG. 1).

Also at box 1187, the oxygen level is select to be 0.5 higher than the current $SPO^2$ level. This means that when the subject is showing excessive response to the hypoxic training stress, the oxygen level is increased to reduce the stress.

At box 1186 the algorithm determines whether the $SPO^2$ level is less than H/02. If it is not, the algorithm moves onwards and eventually back to box 1182. If the $SPO^2$ is less than H/02 the algorithm moves to box 1188 where the normoxic/hypoxic valve 9 is opened for a brief interval which is followed by the algorithm determining at box 1189 whether the $SPO^2$ level has risen above H/01−1. If it has not risen above this level the interval represented by box 1188 is repeated. The action of boxes 1188 and 1189 are to open the hypoxic/normoxic valve 9 until the $SPO^2$ is above H/01−1. When the algorithm determines, at box 1188 that this has eventually occurred, the algorithm proceeds onwards and eventually back to box 82.

In the loop represented by boxes 1188 and 1189 another decision process represented by box 1190 is carried out. At box 1190 the algorithm determines whether the $SPO^2$ has fallen below H/0 min. If it has, the algorithm moves onto box 1191 which represents a brief delay and the algorithm moves onto box 1188. Meanwhile, at box 1192 the algorithm determines whether 5 seconds has passed while the algorithm is in the loop represented by boxes 1189, 1190 and 1191. If this has occurred, the subject will have had an SPO.sup.2 lower titan H/0 min for 5 seconds or more. If that is the case, the algorithm terminates the training session. This termination of the hypoxic training session is a safeguard against a subject suffering ill effects at a blood saturation level that is too low.

After boxes 1186 or 1190, the process returns to box 1182.

Figure 12:
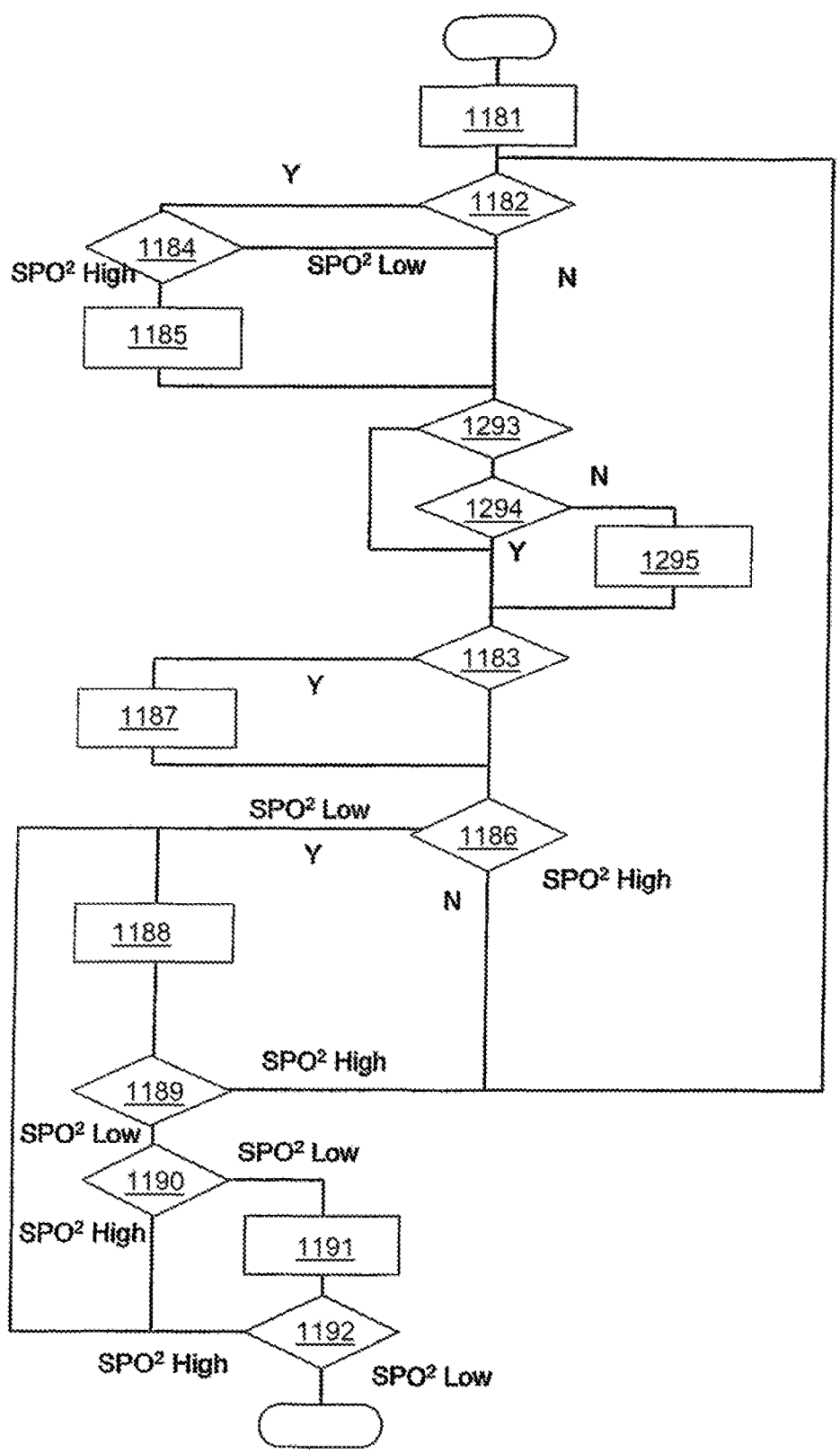
FIG. 12 depicts a process carried out by an alternative embodiment of the present invention to FIGS. 10 and 11, the process controls the normoxic/hypoxic valve and to selection of oxygen contents during intervals of hypoxic air supply.

FIG. 12 depicts a process similar to that depicted in FIG. 11 carried out according to an alternative embodiment of the present invention. The algorithm depicted in FIG. 12 has an additional loop represented by boxes 1193, 1194 and 1195. Box 1193 determines whether a sufficient time interval has passed for SPO.sup.2 levels to taper off. At box 1194 the algorithm determines whether a time dependant fall in SPO.sup.2 levels is tapering off. If it is the algorithm moves on to box 1183. If the SPO.sup.2 levels have not tapered off valve 9 is opened for 5 seconds and the oxygen content is increased by 0.5%. This prevents the subject from responding too aggressively and overshooting target SPO.sup.2 levels, such as H01.

The use of pulse width modulation of a two state valve reduces cost significantly by removing the need for expensive proportional valves and expensive feedback systems, such as those that include oxygen analysers.

The use of a flow control by valves 12 and 21 at both inputs of a venturi 23 allows the circuit 1 to be calibrated for a given oxygen content but also at a given total supply flow rate at the mask 15. Control of the flow rate prevents a subject breathing more air in response to a lower oxygen content in the air they are supplied. This could negate the effect of supplying air with lower oxygen content.

The use of calibrated pulse times of two state valves against oxygen content allows improved feedback response. This is because any feedback based on a pulse oximetry level will not include any response time related to adjustments of values to achieve a suitable oxygen content as supplied to the subject.

The use of $SPO_2$ as an indicator for control of a programme provides a cheaper and/or safer and/or more effective training apparatus.

A two state valve that does not need to have a zero flow state provides a low cost valve for controlling the flow of fluids. More importantly, calibration data for the control of a two state valve allows positive determination of the operation of the valve. This is because a two state valve is unlikely to vary it's characteristics over time, due to mechanical hysteresis and similar effects. Also, pulse width modulation data can be set during a calibration process. Due to the positive determination of the valve states the data will relate consistently over time to a given oxygen content without the need for feedback of oxygen contents. Thus, response times of an oxygen analyser will be eliminated.

Aspects of the present invention have been described by way of example only and it should be appreciated that modifications and additions may be made thereto without departing from the scope thereof.

The invention claimed is:

1. A hypoxic training apparatus which provides gas to an outlet junction, the apparatus comprising:
   a housing comprising a first member and a second member connected by a hinge;
   a gas mixer disposed on the second member of the housing and adapted to mix gas from at least primary and secondary gas supplies to a ratio;
   a gas reservoir connected to the first member and the second member of the housing, and configured to store the mixed gas supplied by the gas mixer and to provide the mixed gas to the outlet junction;
   a tertiary supply gas valve connected to the outlet junction in parallel with the reservoir, wherein the tertiary supply gas valve is adapted to connect the outlet junction to a tertiary supply of gas when gas is not being supplied to the mixer by the primary and/or secondary supply so that the outlet junction is supplied by the tertiary supply of gas and the reservoir until the reservoir is depleted; and
   a controller operatively connected to the gas mixer and adapted to receive a signal indicating a blood oxygen saturation level of a subject from a pulse oximeter, the controller adapted to adjust the ratio of the mixed gas when the blood oxygen saturation level has not reached a first predetermined level of oxygen content within a predetermined time interval, the controller further adapted to read training session data defining any one or any combination of the following parameters associated with an identifier assigned to at least one subject:
      duration of periods of hypoxic supply,
      duration of periods of normoxic supply,
      duration of combined hypoxic and normoxic periods,
      number of sessions of hypoxic and normoxic supply, and
      number of cycles of periods of hypoxic intervals supplied in a given session.

2. The hypoxic training apparatus of claim 1, wherein the secondary and tertiary supplies comprise ambient atmosphere.

3. The hypoxic training apparatus of claim 1, wherein the primary gas supply comprises a supply of nitrogen.

4. The hypoxic training of claim 3, wherein the gas mixer is adapted to mix air at the secondary supply with nitrogen at the primary supply so as to provide air with a given oxygen content.

5. The hypoxic training apparatus of claim 4, wherein the gas mixer is adapted to provide hypoxic air.

6. The hypoxic training apparatus of claim 4, wherein the controller is adapted to control the gas mixer.

7. The hypoxic training apparatus of claim 6, wherein the controller is adapted to read hypoxic training session data which defines intervals of supply of hypoxic air and wherein the controller is also adapted to control the supply of nitrogen to the gas mixer according to the defined intervals.

8. The hypoxic training apparatus of claim 1, wherein the controller is adapted to monitor the signal from the pulse oximeter and to select the ratio so as to provide feedback control of the signal from the pulse oximeter.

9. The hypoxic training apparatus of claim 1, wherein the signal from the pulse oximeter comprises a pulse rate.

10. The hypoxic training apparatus of claim 1, wherein the gas mixer comprises:
    a mixing volume;
    a primary inlet provided for the mixing volume;
    a secondary inlet provided for the mixing volume; and
    an outlet provided for the mixing volume,
    wherein said secondary inlet includes a valve which is adapted to be operated by a pulse width modulation driver adapted to pulse width modulate the valve between two flow states to achieve a given flow state through the secondary inlet.

11. The hypoxic training apparatus of claim 10, wherein said mixing volume comprises a venturi.

12. A hypoxic training apparatus which provides gas to an outlet junction, the apparatus comprising:
- A housing comprising a first member and a second member connected by a hinge;
- a gas mixer disposed on the second member of the housing and adapted to mix gas from at least primary and secondary gas supplies to a given ratio;
- a gas reservoir connected to the first member and the second member of the housing and configured to store the mixed gas supplied by the gas mixer and to provide the mixed gas to the outlet junction;
- a tertiary supply gas valve connected to the outlet junction in parallel with the reservoir, wherein the tertiary supply gas valve is adapted to connect the outlet junction to a tertiary supply of gas when gas is not being supplied to the mixer by the primary supply so that the outlet junction is supplied by the tertiary supply of gas and the reservoir until the reservoir is depleted; and
- a controller operatively connected to the gas mixer and adapted to receive a signal indicating a blood oxygen saturation of a subject from a pulse oximeter, the controller further adapted to shut off the primary supply to the reservoir and open the tertiary supply gas valve when the received signal fails to satisfy a predetermined condition.

13. The hypoxic training apparatus of claim 12, wherein the predetermined condition comprises a blood oxygen level.

14. The hypoxic training apparatus of claim 12, wherein the controller is adapted to select an oxygen content in response to the received signal.

15. The hypoxic training apparatus of claim 12, wherein the controller is further adapted to monitor a rate of change of oxygen content.

16. The hypoxic training apparatus of claim 15, wherein the controller is further adapted to cause the tertiary supply gas valve to open for a predetermined interval when the rate of change of oxygen content is not decreasing.

17. A hypoxic training apparatus which provides gas to an outlet junction, the apparatus comprising:
- a housing comprising a first member and a second member connected by a hinged;
- a gas mixer disposed on the second member of the housing and adapted to mix gas from at least primary and secondary gas supplies to a given ratio;
- a gas reservoir connected to the first member and the second member of the housing and configured to store the mixed gas supplied by the gas mixer, and to provide the mixed gas to the outlet junction;
- a tertiary supply gas valve connected to the outlet junction in parallel with the reservoir, wherein the tertiary supply gas valve is adapted to connect the outlet junction to a tertiary supply of gas when gas is not being supplied to the mixer by the primary supply and/or secondary supply; and
- a controller operatively connected to the gas mixer and adapted to receive a signal indicating a blood oxygen saturation of a subject from a pulse oximeter, the controller further adapted to cause the tertiary supply gas valve to open for a predetermined interval once a first predetermined level of oxygen content is reached and a second predetermined level of oxygen content has not been reached.

* * * * *